United States Patent [19]

Chrespi et al.

[11] Patent Number: 5,726,041
[45] Date of Patent: Mar. 10, 1998

[54] METHOD FOR DETECTING A RECEPTOR-LIGAND COMPLEX USING A CYTOCHROME P450 REPORTER GENE

[75] Inventors: Charles L. Chrespi, Marblehead; Bruce W. Penman, Salem, both of Mass.; Frank J. Gonzalez, Bethesda; Harry V. Gelboin, Chevy Chase, both of Md.; Talia Sher, Rehovot, Israel

[73] Assignees: Gentest Corporation, Woburn, Mass.; The United States of America as represented by the Secretary of the Department of Health and Human Services, Washington, D.C.

[21] Appl. No.: 697,329

[22] Filed: Aug. 22, 1996

Related U.S. Application Data

[60] Provisional application No. 60/002,947, Aug. 30, 1995.

[51] Int. Cl.[6] .................. C12N 15/52; C12N 15/85; C12N 5/22; G01N 33/566
[52] U.S. Cl. .................. 435/69.1; 435/7.1; 435/25; 435/325; 435/372; 435/320.1; 536/23.2; 536/24.1
[58] Field of Search .................. 435/320.1, 325, 435/7.72, 6, 7.8, 7.4, 7.1, 25, 372; 536/24.1, 23.2

[56] References Cited

U.S. PATENT DOCUMENTS

| | | | |
|---|---|---|---|
| 5,023,328 | 6/1991 | Summers et al. | 536/27 |
| 5,155,037 | 10/1992 | Summers | 435/240.2 |
| 5,169,784 | 12/1992 | Summers et al. | 435/320.1 |
| 5,180,666 | 1/1993 | States et al. | 435/29 |
| 5,196,524 | 3/1993 | Gustafson et al. | 536/23.2 |
| 5,215,910 | 6/1993 | Brown et al. | 435/240.2 |
| 5,278,050 | 1/1994 | Summers | 435/69 |
| 5,283,179 | 2/1994 | Wood | 435/8 |
| 5,298,429 | 3/1994 | Evans et al. | 436/501 |
| 5,429,948 | 7/1995 | Crespi et al. | 435/240.2 |
| 5,436,128 | 7/1995 | Harpold et al. | 435/6 |
| 5,478,723 | 12/1995 | Parkinson et al. | 435/4 |

FOREIGN PATENT DOCUMENTS

| | | |
|---|---|---|
| 0 645 459 A1 | 3/1995 | European Pat. Off. |
| 2 269 897 | 2/1994 | United Kingdom |

OTHER PUBLICATIONS

Kliewer et al. (1992) Nature 358: 771–774.

Isabelle Issemann et al., "Activation of a Member of the Steroid Hormone Receptor Superfamily by Peroxisome Proliferators", *Nature*, (1990) 347:645–650.

Colin N.A. Palmer, et al., "Interaction of the Peroxisome Proliferator-Activated Receptor α with the Retinoid X Receptor α Unmasks a Cryptic Peroxisome Proliferator Response Element That Overlaps an ARP-1 Binding Site in the CYP4A6 Promoter", *J. Biol. Chem.* (1994), 269(27):18083–18089.

Jonathan D. Tugwood et al., "The Mouse Peroxisome Proliferator Activated Receptor Recognizes A Response Element In The 5' Flanking Sequence Of the Rate acyl CoA Oxidase Gene", *The EMBO Journal*, (1992), 11(2):433–439.

Yves Boie, et al., "Enantioselective Activation of the Peroxisome Proliferator-Activated Receptor", *The Jrnl. of Bio. Chem.* (1993), 268(8):5530–5534.

Klaus Hoffmann et al., "Stable Chinese Hamster Ovary Reporter Gene Cells Used in Drug Safety and Drug Dev.— The Nonradioactive CAT ELISA", *Biochemica*, (1995), 1:30–32.

Raija L.P. Lindberg et al., "Alteration of Mouse Cytochrome $P450_{coh}$ Substrate Specificity By Mutation of a Single Amino-Acid Residue", *Nature*, (1989), 339:632–634.

Ronald M. Evans, "The Steroid and Thyroid Hormone Receptor Superfamily", *Science*, (1988), 240:889–895.

Keller H. et al., "Signaling Cross-Talk Peroxisome Proliferator-Acivated Receptor Retinoid X Receptor and Estrogen Receptor Through Estrogen Response Elements", *Molecular Endocrinology*, (1995), 9:7;794–804, Abstract.

Palmer CNA, et al., "Novel Sequence Determinants in Peroxisome Proliferator Signaling", *Jrnl. of Biol. Chem.*, (1995), 270(27);16114–16121, Abstract.

Henry K. et al., "Peroxisome Proliferator-Activated Receptor Response Specifities as Defined in Yeast and Mammalian Cell Transcription Assays", *Toxicology & Applied Pharm.*, (1995), 132(2):317–324, Abstract.

Lake BG, "Mechanism of Hepatocarcinogenicity of Peroxisome-Proliferating Drugs and Chemicals [Review]", *Annual Rev. of Pharm. & Toxicology*, (1995), 35:483–507, Abstract.

Bardot O. Clemencet MC, et al., "The Analysis of Modified Peroxisome Proliferator Responsive Elements of the Peroxisomal Bifunctional Enxyme in Transfected HEPG2 Cells Reveals Two Regulatory Motifs", *FEBS Letters*, (1995), 360(2):183–186, Abstract.

Aldridge TC et al., "Identification and Characterization of DNA Elements Implicated in the Regulation of CYP4A1 Transcription", *Biochemical Jrnl.*,(1995), 306 (Part 2):473–479, Abstract.

Krev G. Mahfoudi, et al., "Functional Interactions of Peroxisome Proliferator-Activated Receptor, Retinoid-X Receptor, and SP1 in the Transcriptional Regulation of the Acyl-Coenzyme-A Oxidase Promoter", *Molecular Endocrinology*, (1995), 9(2):219–231, Abstract.

(List continued on next page.)

*Primary Examiner*—Stephen Walsh
*Assistant Examiner*—Michael D. Pak
*Attorney, Agent, or Firm*—Wolf, Greenfield & Sacks, P.C.

[57] ABSTRACT

An improved method for measuring the activity of a promoter sequence in a mammalian cell using a reporter gene is provided. The improvement involves using a reporter cassette containing a DNA sequence encoding a cytochrome P450 with a polyadenylation signal sequence as the reporter gene. Compositions containing the cytochrome P450 reporter cassette also are provided.

5 Claims, 3 Drawing Sheets

OTHER PUBLICATIONS

Huang Q. Yeldandi AV, et al., "Localization of Peroxisome Proliferator-Activated Receptor in Mouse and Rat Tissues and Demonstration of its Nuclear Translocation in Transfected CV-1 Cells", *Intern Jrnl. of Oncology*, (1995), 6(2):307–312, Abstract.

Gulick, T., et al., "The Peroxisome Proliferator-Activated Receptor Regulates Mitochondrial Fatty Acid Oxidative Enzyme Gene Expression", *Proc. Of Nat'l Acad. Sciences of the US,* (1994) 91(23):11012–11016, Abstract.

Mcnae, F., et al., "Molecular Toxicology of Peroxisome Proliferators" *European Journal of Drug Metabolism and Pharmacokinetics*, (1994), 19(3):219–223, Abstract.

Gearing, K.L., et al., "Fatty Acid Activation of the Peroxisome Proliferator Activated Receptor, A Member of the Nuclear Receptor Gene Superfamily", *Journal of Nutrition*, (1994), 124 (8 Suppl S):S1284–1288, Abstract.

Kliewer S.A., et al., "Differential Expression and Activation of a Family of Murine Peroxisome Proliferator–Activated Receptors", *Proc. Nat'l Acad. Sciences of the U.S.*, (1994), 91(15):7355–7359, Abstract.

Asem, Elikplimi K., et al., "Hormone Stimulated Steroid Biosynthesis in Granulosa Cells Studied with a Fluorogenic Probe for Cytochrome $P-450_{scc}$", *J. Steroid Biochem. Molec. Biol.*, 1992, vol. 43, No. 6, pp. 479–487.

Charles L. Crespi, "Xenobiotic-metabolizing Human Cells as Tools for Pharmacological and Toxicological Research", *Advances in Drug Research*, 1995, vol. 26, pp. 179–235.

Nelson, David R., et al., "The P450 Superfamily: Update on New Sequences, Gene Mapping, Accession Numbers, Early Trivial Names of Enzymes, and Nomenclature", *DNA and Cell Biology*, 1993, vol. 12, No. 1, pp. 1–51.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TGACCTNTGT CCT                                         13

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TCAACTNTGC CCT                                         13

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CTAGAGGGGG ATTTCCAAGA GGCCACCTGG CAGTTGC    37

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

CTAGGCAACT GCCACCTGGC CTCTTGGAAA TCCCCCT    37

( 2 ) INFORMATION FOR SEQ ID NO:5:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AGCTTACGCA AACACTGAAC TAGGGCAAAG TTGAGGGCAG TGAACTAGGG CAAAGTTGAG    60

GGCAGTGAAC TAGGGCAAAG TTGAGGCAG    89

( 2 ) INFORMATION FOR SEQ ID NO:6:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:6:

TCGACTGCCT CAACTTTGCC CTAGTTCACT GCCGTCAACT TGCCCTAGT TCACTGCCCT    60

CAACTTTGCC CTAGTTCAGT GTTTGCGTA    89

( 2 ) INFORMATION FOR SEQ ID NO:7:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

| | | | | | |
|---|---|---|---|---|---|
| TACAGAGGTT | GTGAGCCCCC | ATGTGGTTGC | TGGGAATTGA | ACTCAGGACA | ATGAACCCTT | 60
| TCCCGAACGT | GACCTTTGTC | CTGGTCCCCT | TTTGCTCCTA | TTTGGTTAGG | TTCCAGTAAA | 120
| ATCAACAGTT | CCAGTAAATT | CCCCTATTAG | CCTCTTCACT | CCGCCCGA | | 168

( 2 ) INFORMATION FOR SEQ ID NO:8:

( i ) SEQUENCE CHARACTERISTICS:
        ( A ) LENGTH: 251 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

| | | | | | |
|---|---|---|---|---|---|
| CAGCTGCTTC | ATCCCCGTGG | CCCGTTGCTC | GCGTTTGCTG | GCGGTGTCCC | CGGAAGAAAT | 60
| ATATTTGCAT | GTCTTTAGTT | CTATGATGAC | ACAAACCCCG | CCCAGCGTCT | TGTCATTGGC | 120
| GAATTCGAAC | ACGCAGATGC | AGTCGGGGCG | GCGCGGTCCG | AGGTCCACTT | CGCATATTAA | 180
| GGTGACGCGT | GTGGCCTCGA | ACACCGAGCG | ACCCTGCAGC | GACCCGCTTA | ACAGCGTCAA | 240
| CGCGTGCCGC | A | | | | | 251

( 2 ) INFORMATION FOR SEQ ID NO:9:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

| | | | | | |
|---|---|---|---|---|---|
| GTAAGTTTTT | GGTTACAAAC | TGTTCTTAAA | ACGAGGATGT | GAGACAAGTG | CTTTCCTGAC | 60
| TTGGTTTGGT | ATCAAAGGTT | CTGATCTGAG | CTCTGAGTGT | TCTATTTTCC | TATGTTCTTT | 120
| TGGAATTTAT | CCAAATCTTA | TGTAAATGCT | TATGTAAACC | AAGATATAAA | AGAGTGCTGA | 180
| TTTTTTGAGT | AAACTTGCAA | CAGTCCTAAC | ATTCACCTCT | TGTGTG | | 226

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:10:

| | | | | | |
|---|---|---|---|---|---|
| AGCTTGTCGA | CGATATCACT | AGTTCTAGAA | GATCTCTGCA | GACGCGTTGA | TCACCGCGGG | 60

( 2 ) INFORMATION FOR SEQ ID NO:11:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: NO ( x i ) SEQUENCE DESCRIPTION: SEQ ID NO:11:

AATTCTAGAC TCGAGAAGCT T                                              21

( 2 ) INFORMATION FOR SEQ ID NO:12:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: YES ( x i ) SEQUENCE DESCRIPTION: SEQ ID NO:12:

GATCAAGCTT CTCGAGTCTA G                                              21

( 2 ) INFORMATION FOR SEQ ID NO:13:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: NO ( x i ) SEQUENCE DESCRIPTION: SEQ ID NO:13:

CAGCGGCCGA GCTAGCAGAT CTCCTAGGTA TCGAT                               35

( 2 ) INFORMATION FOR SEQ ID NO:14:

( i ) SEQUENCE CHARACTERISTICS:
      ( A ) LENGTH: 44 base pairs
      ( B ) TYPE: nucleic acid
      ( C ) STRANDEDNESS: single
      ( D ) TOPOLOGY: linear ( i i i ) HYPOTHETICAL: NO ( i v ) ANTI-SENSE: YES ( x i ) SEQUENCE DESCRIPTION: SEQ ID NO:14:

AGCTATCGAT ACCTAGGAGA TCTGCTAGCT GCGGCCGCTG GTAC                     44

( 2 ) INFORMATION FOR SEQ ID NO:15:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO (i v) ANTI-SENSE: NO (x i) SEQUENCE DESCRIPTION: SEQ ID NO:15:

CCGGTACCTA CAGAGGTTGT GAGCC                                     25

(2) INFORMATION FOR SEQ ID NO:16:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:16:

CGGGTACCAT CGGGCGGAGT GAAGAGGCTA ATA                            33

METHOD FOR DETECTING A RECEPTOR-LIGAND COMPLEX USING A CYTOCHROME P450 REPORTER GENE

This application was supported at least in part by a contract from the National Institutes of Health (NIEHS) Contract No. N43-ES-21003 and N44-ES-32003. The government has certain rights in this invention.

This application claims priority to the United States provisional application Ser. No. 60/002,947, filed Aug. 30, 1995, the entire contents of which are incorporated herein by reference.

FIELD OF THE INVENTION

This invention relates to methods and compositions in which a cytochrome P450 gene is used as a reporter gene to measure the activity of a promoter sequence.

BACKGROUND OF THE INVENTION

The use of reporter genes to measure the relative activity of a promoter sequence is well known (see, e.g., Molecular Cloning, second edition, editor J. Sanbrook et al., Cold Spring Harbor Laboratory Press (1989)). Although not technically precise, for simplicity of discussion, the phrase "reporter gene" as used herein is meant to embrace genomic DNA sequences ("genes"), as well as cDNAs which encode the reporter gene product. Assays for measuring the relative activity of a promoter are useful for identifying and obtaining promoter sequences that promote the expression of particular genes in a host organism. In general, a reporter gene is fused to a promoter of interest and the amount of reporter gene product produced is indicative of the relative activity of the promoter. Ideally, the reporter gene product is easily assayed and has an activity which is not normally found in the organism of interest.

Chloramphenicol acetyl transferase (CAT) is commonly used as a reporter gene in mammalian cell systems because mammalian cells do not have detectable levels of this activity. The assay for CAT involves incubating cellular extracts with radiolabeled chloramphenicol and appropriate co-factors, separating the starting materials from the product by, for example, thin layer chromatography (TLC), followed by autoradiography or quantitation of the radiolabeled product by scintillation counting. Other reporter gene assays for enzymes such as luciferase, beta-galactosidase and alkaline phosphatase also are labor intensive. While assays for these enzymes as reporter genes are widely used, a reporter system which does not require cell processing, radioisotopes and chromatographic separations would be much more amenable to automation.

In addition to using reporter genes for studying gene regulation in general, reporter genes also have been used to measure the activation of a member of the steroid hormone receptor superfamily by peroxisome proliferators (I. Issemann and S. Green, Nature 347:645–650 (1990)). The peroxisome proliferators are a diverse group of chemicals which include hypolipodemic drugs, herbicides and plastisizers (reviewed in J. K. Reddy and N. D. Lalwani, CRC Writ. Rev. Toxicol. 12:1–58 (1983), J. K. Reddy and M. S. Rao, TIPS 438–443 (1986)). These agents induce hepatomegaly and hepatic peroxisome proliferation in rodents. Increased transcription of genes required for the peroxisomal B-oxidation of long chain fatty acids in response to peroxisome proliferators also has been reported. It is generally believed that the peroxisome proliferators do not directly interact with or damage DNA, but rather induce carcinogenicity via an indirect mechanism which may not involve covalent DNA binding.

Given the toxicological importance of peroxisome proliferators and the diverse chemical agents which induce this effect, a versatile, sensitive, easily automated, mechanism-based system for detecting agents which induce peroxisome proliferation is desirable. This system would have important screening applications in new chemical discovery and development, as well as in safety assessment for new and existing chemicals.

SUMMARY OF THE INVENTION

In its broadest aspect, the invention is directed to methods and compositions for measuring the activity of a promoter sequence in a mammalian cell. The methods involve substituting a DNA sequence encoding a cytochrome P450 for a known reporter gene of the prior art (e.g., CAT, luciferase) and measuring the relative activity of the promoter by measuring the catalytic activity of the expressed cytochrome P450 protein. According to a more narrow aspect, the invention is directed to methods and compositions for measuring activation of a member of the steroid hormone receptor superfamily. According to a still more narrow aspect, the invention is directed to methods and compositions for measuring the activation of a peroxisome proliferator activator receptor by peroxisome proliferators.

According to one aspect of the invention, an improved method for measuring the activity of a promoter sequence in a mammalian cell is provided. The improved method involves using a novel reporter cassette containing a DNA sequence encoding a cytochrome P450 (e.g., a cDNA or a gene encoding a cytochrome P450) as a reporter gene operatively coupled to a promoter sequence. The reporter cassette further includes a polyadenylation signal sequence to permit successful transcription of the reporter gene into a functional mRNA for protein translation. Thus, as used herein, the reporter cassette of the invention serves as an expression cassette for expressing the cytochrome P450 gene.

The reporter cassette of the invention can be substituted for the reporter cassettes that have been described in the prior art for measuring the activity of a promoter sequence. Exemplary reporter genes of the prior art for which a DNA encoding a cytochrome P450 can be substituted are described in U.S. Pat. No. 5,196,524, issued to Gustafson et al., entitled "Fusion Reporter Gene For Bacterial Luciferase (GUSTAFSON); U.S. Pat. No. 5,283,179, issued to Wood, entitled "Luciferase Assay Method" (WOOD); U.S. Pat. No. 5,436,128, issued to Harpold et al., entitled "Assay Method and Compositions for Detecting and Evaluating the Intracellular Transduction of an Extracellular Signal" (HARPOLD); U.S. Pat. No. 5,298,429, issued to Evans et al., entitled "Bioassay for Identifying Ligands for Steroid Hormone Receptors" (EVANS); and U.S. Pat. No. 5,215,910, issued to Brown et al., entitled "Host Cells Transformed with Sterol Regulatory Elements" (BROWN).

In contrast to the reporter genes of the prior art, the claimed invention advantageously provides a method for measuring the activity of a promoter sequence in intact mammalian cells that contain a cytochrome P450 catalysis system using real time light (fluorescence) measurements. Virtually all mammalian cells contain the requisite cytochrome P450 catalysis system. Thus, the invention eliminates many of the labor-intensive aspects (e.g., cell lysis and separation of cellular components) that generally are required to practice the prior art methods for measuring the activity of a promoter sequence in a mammalian cell.

According to yet another aspect of the invention, a method for detecting the formation of a receptor-ligand complex in a mammalian cell is provided. The cell contains the above-described reporter cassette for detecting formation of the receptor-ligand complex and a cytochrome P450 catalysis system. The reporter cassette includes a DNA sequence encoding a cytochrome P450 with a polyadenylation signal sequence operatively coupled to a promoter sequence and a DNA-responsive (response) element that is responsive to (i.e., binds to) a DNA binding element present in the receptor-ligand complex. The method for detecting the formation of the receptor ligand complex involves: (1) contacting a ligand with a cell that expresses a receptor specifically reactive with the ligand under conditions to permit formation of the receptor ligand complex; (2) contacting the cell with a substrate (e.g., coumarin) for the cytochrome P450 catalysis system under conditions to permit catalysis of the substrate by the cytochrome P450 catalysis system to form a cytochrome P450 catalysis system product (e.g., 7-hydroxycoumarin); and (3) detecting the cytochrome P450 catalysis system product. The formation of the cytochrome P450 catalysis system product is indicative of the formation of the receptor-ligand complex. According to a particularly preferred aspect of the invention, the above disclosed method is useful for detecting the activation of PPARα by peroxisome proliferators.

According to yet other aspects of the invention, various novel compositions that are useful for practicing the foregoing methods are provided. These include the above-described reporter cassette, a vector (e.g., plasmid) containing the cassette, a cell transformed or transfected by the reporter cassette or by the vector containing the cassette, and a host cell transformed or transfected by the reporter cassette or by the vector containing the reporter cassette. Novel compositions containing a receptor cassette (described below), as well as plasmids and cells containing the same, also are provided. The nucleic acid cassettes can be prepared in large quantities by, for example, transforming or transfecting a bacterial cell with a plasmid vector containing the reporter cassette, allowing the cell to divide and isolating multiple copies of the reporter cassette from the cells according to procedures well known to those of ordinary skill in the art. In a particularly preferred embodiment, the reporter cassette includes a single DNA encoding a cytochrome P450 operatively coupled to the promoter sequence.

A host cell transformed or transfected with the reporter cassette or a plasmid vector containing the same also are disclosed herein. The host cell contains a DNA sequence encoding a receptor specific for a ligand (i.e., the receptor specifically reacts with the ligand to form the receptor-ligand complex which affects the activity of the promoter sequence) and a cytochrome P450 catalysis system. The DNA encoding the receptor with a polyadenylation signal sequence can be contained on a cassette on a plasmid (the same or a different plasmid containing the reporter cassette) or can be contained on the host cell chromosomal DNA.

The host cell further contains a cytochrome P450 catalysis system. As used herein, the cytochrome P450 catalysis system refers to the complement of metabolic enzymes that are necessary to support cytochrome P450 catalytic function. These enzymes consist principally of the NADPH cytochrome P450 oxido reductase and cytochrome $b_5$. Cytochrome $b_5$ stimulates the catalytic activity of a subset of P450 enzymes (see e.g., "Cytochrome P450" in *Methods in Enzymology*, vol. 206, ed. M. Waterman and E. Johnson, Academic Press, Inc., New York, N.Y. (1991)). Host cells containing a cytochrome P450 catalysis system include virtually all mammalian cell types (e.g., lymphoblasts, fibroblasts, epithelial cells, HeLa cells and HepG2 cells).

In a particularly preferred embodiment, the host cell is a lymphoblast, the receptor is a peroxisome proliferator activator receptor (PPARα), and the reporter cassette contains: a minimal promoter, a DNA responsive element (e.g., a portion of the rat acetyl CoA oxidase gene), a DNA sequence encoding human CYP2A6 or mouse CYP2A5, and a polyadenylation signal sequence. In an alternative embodiment, the DNA sequence encodes a modified form of mouse CYP2A4. The modified form of mouse CYP2A4, referred to herein as "mouse mCYP2A4," has a single amino acid residue change with respect to the natural product. This amino acid change confers coumarin 7-hydroxylase activity upon the modified enzyme. The mouse mCYP2A4 is described by R. Lindberg and M. Negishi in *Nature* 339:632–634 (1989).

These and other aspects of the invention, as well as various advantages and utilities will be more apparent with reference to the detailed description of the preferred embodiments and in the accompanying Examples.

Each of the patents, patent publications and literature references identified herein is incorporated in its entirety herein by reference.

DETAILED DESCRIPTION

Figure 1:
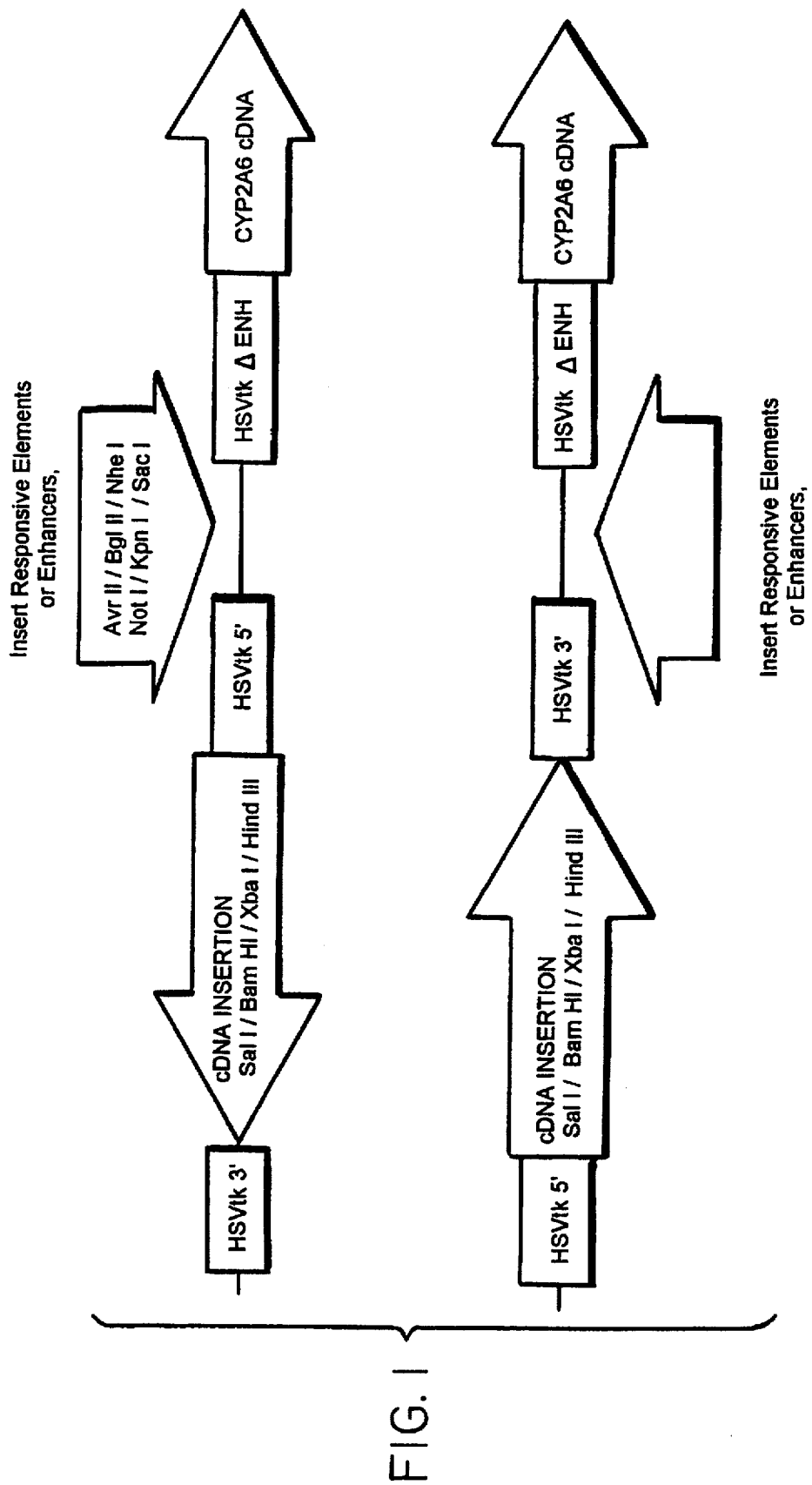
FIG. 1. Schematic diagrams of the cDNA insertion and reporter portions of p2A6p1TK derivatives. The remaining portion of the plasmid contains the OriP sequences and the genes conferring resistance to hygromycin B and ampicillin. Upper diagram is isolate "414" lower diagram is isolate "1212". These two isolates differ only in the orientation of the HSVtk expression unit.

An improved method for measuring the activity of a promoter sequence in a mammalian cell is disclosed herein. The improvement involves using a DNA sequence encoding a cytochrome P450 as a reporter gene.

The cytochrome P450s are a large family of hemoproteins capable of metabolizing xenobiotics such as drugs, procarcinogens and environmental pollutants as well as endobiotics such as steroids, fatty acids and prostaglandins (reviewed in, e.g., Nelson, et al., *DNA Cell Biol.* 12:1–15 (1993)). Several laboratories have successfully transfected single cytochrome P450 cDNAs into mammalian cell lines. More recently, a lymphoblast cell line transfected with a multiplicity of cytochrome P450s (referred to as the "MCL-5" cell line) also has been described. (See, U.S. Pat. No. 5,429,948, issued to Crespi et al.). The MCL-5 cell line is useful for mutagenicity testing of putative carcinogens. Despite the extensive use of the cytochrome P450s as agents for mutagenicity testing and for studying drug metabolism, the literature is silent with respect to the use of any cytochrome P450 gene as a reporter gene for assessing the activity of a promoter sequence.

The preferred DNA sequence for the reporter gene of the invention encodes a cytochrome P450 with a polyadenylation signal sequence which, in combination with the host cell cytochrome P450 catalysis system, catalyzes the conversion of a catalysis system substrate to a fluorometric cytochrome P450 catalysis system product. As used herein, the cytochrome P450 catalysis system refers to the collection of enzymes which collectively support cytochrome P450 catalytic function. These enzymes are well-known in the art and consist principally of the NADPH cytochrome P450 oxido reductase and cytochrome $b_5$. See e.g., "Biotransformations: The Cytochromes P450," chapter 23 in *Textbook of Biochemistry*, ed. T. Devlin, Wiley-Liss, New York, N.Y. (1992) and *Methods in Enzymology*, vol. 206 (1991) supra. Accordingly, as used herein, a cytochrome P450 catalysis system substrate refers to an enzyme substrate which is acted upon by the catalysis system enzymes, together with the cytochrome P450, to form an enzyme reaction product (i.e., the catalysis system product).

In the preferred embodiments, the catalysis system substrate is coumarin or a fluorescent molecule that is converted to an easily detectable, fluorescent product (e.g., 7-hydroxycoumarin). Fluorescent substrates have excitation and emission wavelengths that are different from the excitation and emission wavelengths of the fluorescent product. For example, the substrate can be a substituted coumarin, an unsubstituted coumarin, a substituted resorufin or a phenoxazine-3-one. Exemplary cytochrome P450 catalysis system substrates whose products are fluorometric include coumarin, 3-cyanocoumarin, 4-methylcoumarin, 4-trifluoromethylcoumarin, 7-alkoxycoumarin, 7-alkoxy-3-cyanocoumarin, 7-alkoxy-4-methylcoumarin, 7-alkoxy-4-trifluoromethylcoumarin, 7-alkoxyresorufin and phenoxazin-3-one. These and other suitable substrates are available from Molecular Probes (Eugene, Oreg.), Enzyme Systems Products (Livermore, Calif.) and Sigma Chemical Co. (St. Louis, Mo.). In the more preferred embodiments, the substrate is a substituted or unsubstituted coumarin, most preferably, an unsubstituted coumarin.

Virtually all mammalian cells contain a cytochrome P450 catalysis system that can support cytochrome P450 catalytic function. Accordingly, it is believed that a DNA sequence encoding a cytochrome P450 can be used as a reporter gene for measuring promoter activity in virtually all mammalian cell types, although the degree of efficacy may vary between different cell types. In the most preferred embodiments, the DNA sequence encoding a cytochrome P450 is used as a reporter gene in human cell lines (e.g., a lymphoblast, a fibroblast, an epithelial cell, a HeLa cell, and a HepG2 cell). However, the DNA sequence encoding a cytochrome P450 also is useful as a reporter gene in a wide variety of non-human, mammalian cells (e.g., CHO cells, COS-1 cells, V79 cells, 3T3 cells, L5178Y mouse lymphoma cells and MDCK cells).

The AHH-1 TK±-cell line of human B-lymphoblastoid cells, a derivative of AHH-1 (ATCC Accession No. CRL8146) are the preferred host cells for practicing the invention. This cell line grows well in suspension culture and forms colonies at high efficiency. AHH-1 TK±-cells have been used in combination with extrachromosomal vectors containing the OriP sequences derived from Epstein Barr virus (EBV). Engineered-derivatives of AHH-1 TK±-expressing xenobiotic metabolizing enzymes previously have been described (U.S. Pat. No. 5,429,948 issued to Crespi et al.). A human B lymphoblastoid cell line, strain AHH-1 TK±-with plasmid pT 194/T144 296 MSV #39 was received by to the ATCC, Rockville, Md., on Aug. 30, 1995, and assigned ATCC accession number CRL 11978.

The invention is meant to embrace compositions and methods in which a DNA sequence encodes any cytochrome P450 currently known or discovered in future. As will be immediately apparent to one of skill in the art, the essence of the invention is the discovery that a DNA sequence (cDNA or gene) encoding a cytochrome P450 can be used as a reporter gene to measure the activity of a promoter sequence. Accordingly, the invention should not be construed as being limited to a particular construct encoding a specific cytochrome P450. It should further be noted that the nomenclature of the cytochrome P450s has changed significantly over the last several years and that, in particular, cytochrome P4502A6 ("CYP2A6") (described in the Examples) originally was referred to as CYPIIA2, then CYPIIA3. This evolution in nomenclature is described in the following references: Nebert, D., et al., "The P450 Gene Superfamily: Recommended Nomenclature", *DNA* 6(1): 1–11 (1987); Nebert, D., et al., "The P450 Superfamily: Updated Listing of All Genes and Recommended Nomenclature for the Chromosomal Loci", *DNA* 8(1):1–13 (1989); and Nebert, D., et al., "Update on New Sequences, Gene Mapping, and Recommended Nomenclature", *DNA and Cell Biology* 10(1):1–14 (1991).

In the preferred embodiments, the DNA sequence encodes one of following cytochrome P450s: human CYP2A6, human CYP1A1, human CYP1A2, human CYP2B6, human CYP2D6, human CYP2E1, rat CYP1A1, rat CYP1A2, rat CYP2E1, mouse CYP2A5, mouse mCYP2 A4, mouse CYP1A1, mouse CYP1A2, and mouse CYP2E1. Each of these cytochrome P450s, together with a cell having the requisite cytochrome P450 catalysis system, catalyzes the conversion of a cytochrome P450 catalysis system substrate to a detectable cytochrome P450 catalysis system product. In the particularly preferred embodiments, the DNA sequence encodes human CYP2A6 or mouse CYP2A5 and coumarin serves as the catalysis system substrate.

CYP2A6 is the human coumarin 7-hydroxylase (Yamano et al., *Biochemistry* 29:1322–1329 (1990)). In a host cell containing a cytochrome P450 catalysis system, this enzyme efficiently converts the non-fluorescent substrate, coumarin (unsubstituted), to the highly fluorescent product, 7-hydroxycoumarin. The apparent $K_m$ is 1 uM. The Stokes shift is very large with excitation at 368 nm and emission at 456 nm. As described in the Examples, the product is stable under physiological conditions and reporter enzyme activity can be assayed in whole cells. The Examples further demonstrate that incubation of the host cell containing a reporter cassette which includes a DNA sequence encoding CYP2A6 with the coumarin substrate (2 days at $2 \times 10^6$ cells per ml) results in linear cytochrome P450 catalysis system product formation. Moreover, the assay is quite sensitive and can detect less than 1 pmole product. Indeed, the assay has sufficient sensitivity to permit the direct visual detection (as a blue fluorescence) of product formation (positive responses) in a microtiter plate under 360 nm (UVA) light exposure. The assay components of the Examples (e.g., reporter cassettes, host cells containing the reporter cassettes) can easily be standardized and incorporated into a kit for detecting novel promoters and/or for measuring the activity of promoter sequences.

At a minimum, the reporter cassette contains a DNA sequence (a cDNA or a gene) encoding the reporter protein (in this case a cytochrome P450) operatively coupled to a promoter sequence, and a polyadenylation signal sequence. In the Examples, the polyadenylation signal (present at the 3' end of the DNA sequence encoding the CYP2A6 reporter gene) is derived from the plasmid from which the CYP2A6 cDNA is derived. The phrase "operatively coupled" means that the transcriptional activity of the promoter sequence determines the level of transcription of the DNA sequence encoding the cytochrome P450. This minimal reporter cassette construct is useful for identifying novel promoters.

Optionally, the reporter cassette further includes an enhancer element, operatively coupled to the promoter sequence, for increasing the transcriptional activity of the promoter sequence. Exemplary enhancer elements are disclosed in the Examples. An enhancer element increases the level of transcription in the cell. The enhancer element can be trans-acting, i.e., present in a nucleic acid sequence other than that of the reporter cassette if a protein is produced but is usually cis-acting, i.e., present on the same DNA sequence as the reporter cassette. The Examples suggest that the Harvey Murine Sarcoma Virus enhancer provides the greatest enhancement of transcription when used in combination with a reporter cassette containing a minimal promoter, a DNA responsive element suitable for measuring the peroxisome proliferator activator receptor and a DNA sequence encoding a cytochrome P450 (CYP2A6) in AHH-1 TK± cells.

Reporter cassettes (with or without the enhancer element) for measuring the activation of a receptor, can further include a DNA-responsive element that is responsive to the receptor-ligand complex (i.e., the receptor-ligand complex contains a DNA-binding element which can interact directly with the DNA responsive element). As will be immediately apparent to those skilled in the art, selection of the DNA responsive element for inclusion in the reporter cassette is dictated by the identity of the receptor. The nucleic acid sequence for any particular DNA responsive element can be determined for any gene (the transcription of which is directly regulated by a receptor-ligand complex) using no more than routine experimentation. For example, the cytochrome P450 reporter cassettes can be used in a "shotgun" approach to identify novel DNA responsive elements for a particular receptor by, e.g., inserting fragments of DNA (which are suspected of containing a responsive element) into the reporter cassette (at a position between the enhancer and a minimal promoter) to form a plurality of putative responsive element-containing cassettes, at least some of which should contain the suspected DNA responsive element. These putative responsive element-containing cassettes then are introduced into cells, the cells are plated in the presence of coumarin and the ligand of the receptor, colonies which fluoresce are selected and the DNA contained therein is characterized (e.g., sequencing the DNA cassette) to definitively identify a novel DNA responsive element.

For each gene under receptor-ligand transcriptional control, the sequence of the DNA responsive element is that portion of the promoter (of the gene under receptor-ligand transcriptional control) with which the receptor-ligand complex specifically interacts. In reference to the preferred embodiment for measuring activation of a PPARα, the phrase "responsive to a DNA-binding element" means that the DNA-binding element contained in the PPARα specifically interacts with the DNA-responsive element in the reporter cassette and by so doing, modulates (increases or decreases) the level of transcription of the reporter gene. In the particularly preferred embodiment for measuring activation of the PPARα, the DNA sequence encodes human CYP2A6, mouse CYP2A5, or mouse mCYP2A4.

DNA-responsive elements for the PPARα have been described. (See, e.g., C. Palmer et al., *J. Biol. Chem.* 27:18083-18089 (1994)). The mouse PPARα contains a DNA-binding element which recognizes a DNA responsive element in the 5' flanking sequence of the rat acyl CoA oxidase gene (J. Tugwood et al., *EMBO J.* 11(2):433-439 (1992)). A fragment of the rat acyl CoA gene (-472 to -640) containing the DNA responsive element has been incorporated into a particularly preferred reporter cassette of the invention (see the Examples). This DNA-binding element also recognizes a DNA responsive element in the rabbit CYP4A6 gene (JCO-PPRE; Muerhoff et al., *J. Biol. Chem.* 267:19051-19053 (1992)). The reporter construct containing the ACO-PPRE included a minimal HSVtk promoter, an SV40 enhancer and the mouse PPARα. An alternative reporter construct containing the JCO-PPRE, included a MMTV-LTR minimal promoter and the SV40 enhancer, i.e., this construct was essentially identical to the ACO-PPRE-containing reporter construct with the exception that JCO-PPRE was substituted for the ACO-PPRE and the minimal MMTV-LTR promoter was substituted for the HSVtk#7 promoter. Each of these constructs has been used to measure peroxisome proliferator-induced activation of a PPARα. DNA-responsive elements for other members of the steroid hormone receptor super family (e.g., the receptors for glucocorticoid and estrogen) can be identified using methods similar to those described in the above-cited references for identifying the DNA responsive element for PPARα.

The ACO-PPRE used in Example 1 contained a single copy of the core sequence TGACCTNTGTCCT (SEQ. ID No. 1) and was isolated by PCR using oligo primers bracketing sequences -472 to -640 of the rat acyl CoA oxidase gene (Tugwood et al., *EMBO J.* 11:433-439 (1992)). The rabbit CYP4A6-derived (Muerhoffet al., *J. Biol. Chem.* 267:19051-19053 (1992)) JCO-PPRE oligonucleotide contained three copies of the core sequence TCAACTNTGC-CCT (SEQ. ID No. 2). These elements reportedly work in either orientation (Muerhoff et al., *J. Biol. Chem.* 267:19051-19053 (1992)). When these two PPREs were coupled to a minimal MMTV-LTR promoter and cotransfected with a mPPAR, both PPREs were functional and the JCO-PPRE reportedly appeared to be slightly better than the ACO-PPRE.

One general approach to improving the responsiveness of promoters in the claimed methods is to include multiple response elements in the reporter cassette. The Examples show that the responsiveness of the reporter gene can be increased by incorporating 2, 3 or 4 PPREs in the reporter cassette. However, it is believed that in the preferred embodiments, reporter cassettes should contain about 30 bp between PPREs to minimize the affect of steric constraints on the ability of multiple PPREs to interact with the receptor-ligand complex. Kliewer et al., *Nature* 358:771-774 (1992) reported a 29 bp separation and Muerhoffet al., *J. Biol. Chem.* 267:19051-19053(1992) reported a 23 bp separation and reported substantial improvements with multiple PPRE.

In the preferred embodiments, the reporter cassette contains a minimal promoter, i.e., a promoter which supports very low or negligible transcription in the absence of other elements (e.g., enhancers, DNA response elements). The most minimal promoter is a TATA box. The Examples describe reporter cassettes for measuring receptor-ligand complex-mediated promoter sequence activation that have been constructed using two different truncated and hence "minimal" promoters, the HSVtk and MMTV LTR. Two different truncations of the HSVtk, one more minimal than the other, also have been constructed and evaluated in a model assay (the assay for activation of the peroxisome proliferator activator receptor (PPARα)).

Alternatively, promoters such as the SV40 early promoter or the cytomegalovirus (CMV) early intermediate promoter can be used if lower expression levels of the reporter enzyme or receptor are needed to overcome, e.g., toxicity or instability associated with very high expression levels of the receptor. For example, putative promoters which may be useful in combination with the cytochrome P450 reporter gene can be identified using no more than routine experimentation, e.g., by substituting a putative promoter for the HSVtk promoter in the preferred reporter cassette embodiment and determining the affect of this substitution on the catalytic activity of the reporter enzyme. Other promoters which have been used in mammalian cells also are believed to be useful in combination with the cytochrome P450 reporter genes disclosed herein.

The response of the reporter gene primarily is affected by the intracellular concentration of the receptor-ligand complex. Accordingly, the response of the reporter gene to a particular ligand can be increased by increasing the concentration of the ligand (with constant receptor levels) or by increasing the concentration of the receptor (with constant ligand levels). Given the cytotoxicity (and associated inhibition of gross reporter function) of some ligands, increasing receptor concentration is the preferred method for increasing the response of the cytochrome P450 reporter gene system. Several different approaches can be used to increase receptor concentrations, including the use of stronger promoters in the receptor cassette, multiple receptor cassettes and inclusion of the reporter cassette on a high copy number vector. Receptor expression levels can be directly quantitated by immunoassay using specific antibodies to the receptor or indirectly measured (e.g., by measuring reporter enzyme catalytic activity as described above).

The cytochrome P450 reporter genes are useful for measuring the formation of a receptor-ligand complex, provided that the receptor-ligand complex contains a DNA binding element (which interacts directly with a DNA responsive element present in the reporter cassette) to modulate promoter sequence activity. As used herein, "receptor activation" refers to the process during which the ligand specifically interacts with the receptor to form a receptor-ligand complex which, in turn, modulates promoter sequence activity by directly interacting with a DNA responsive element present in the reporter cassette. The reporter cassettes disclosed herein are particularly useful for measuring activation by peroxisome proliferators of receptors of the steroid hormone receptor superfamily (e.g., PPARα) and receptors having sequence homology to those in this superfamily (e.g., the Aryl hydrocarbon receptor which serves as a receptor for dioxin). The steroid and thyroid hormone receptor superfamily is reviewed by R. Evans in *Science* 240:889–894 (1988).

A DNA sequence encoding a cytochrome P450 (human CYP2A6) was used as a reporter gene to measure receptor ligand complex formation for several naturally occurring (i.e., native to host cell) and three chimeric receptors in a human cell line. Each of the chimeric receptors contained the DNA binding element of the rat glucocorticoid receptor ("GR") (Miesfeid et al., *Cell* 46:389–399 (1986)) obtained from G. Hager), including base pairs 46 to 1563 but with ligand binding regions originating from three different species to form each of the three chimeric receptors. To produce the chimeras, the rat GR DNA binding element was modified by the insertion of a Xho I site after bp 1563 in each of the PPARα cDNAs between amino acid 166 and 167 (see, e.g., Issemann and Green, *Nature* 347:645–650 (1990)). The sequences for the three ligand binding domains for three different species are:

(1) Mouse PPARα ligand binding domain (498–1407 bp). [This ligand binding domain was obtained from mouse liver total RNA by cDNA synthesis and PCR. Primers were based on the published mouse PPARα sequence (I. Issemann and S. Green, *Nature* 347:645–650 (1990))].

(2) Rat PPARα ligand binding domain (498–1407 bp). [This ligand binding domain was obtained from total RNA from FAO cells induced with 0.1 mM clofibrate prior to RNA extraction using cDNA synthesis and PCR].

(3) Human PPARα ligand binding domain (498–1407 bp) obtained from a human liver cDNA library using the mouse PPARα cDNA as probe.

A detailed description of the assay for measuring the receptor (e.g., PPARα) activation by peroxisome proliferators is provided in the Examples. This assay can be used as a model assay for measuring the activation of any receptor that is responsive to a peroxisome proliferator, provided that the receptor contains a DNA binding element which specifically interacts with a DNA responsive element contained in the reporter cassette. In general, the methods disclosed herein are useful for measuring activation of the promoter sequence by direct interaction between a DNA responsive element that is present in a reporter cassette and a DNA-binding element that is present in the receptor.

The assay for measuring receptor-ligand complex formation (and hence, complex-mediated promoter sequence activation) involves: (1) contacting a ligand with a cell that expresses a receptor specifically reactive with the ligand, under conditions to permit formation of the receptor-ligand complex; (2) contacting the cell with a substrate for the cytochrome P450 catalysis system under conditions to permit catalysis of the substrate by the cytochrome P450 catalysis system to form a cytochrome P450 catalysis system product; and (3) detecting the cytochrome P450 catalysis system product. The formation of the cytochrome P450 catalysis system product is indicative of the formation of the receptor-ligand complex, which in turn, is indicative of receptor-ligand complex-mediated promoter sequence activation.

In general, the conditions for contacting the cell with the substrate to permit cytochrome P450 catalysis system catalysis of the substrate include adding the substrate (e.g., coumarin) to cell culture media containing between about $1 \times 10^5$ to about $5 \times 10^6$ cells/ml and incubating the culture (containing the cells and substrate) at about 37° C. for between about 0.25 hours to about 3 days. Routine experimentation can be used to select the optimal cell numbers, substrate concentration and incubation time for any particular reporter enzyme. Of course, the optimal parameters also will depend upon the Km of the enzyme. Thus, in general, if the cells used for the assays described herein express low levels of a cytochrome P450 gene or express a reporter gene having a low catalytic activity, more cells can be used in the assay to achieve the desired result, i.e., an assay having sufficient sensitivity and reproducibility for measuring activation of a promoter sequence in an intact mammalian cell.

Exemplary conditions for contacting a lymphoblast cell that has been transfected with a reporter cassette containing a minimal promoter, a DNA responsive element for a PPARα (a fragment containing −472 to −640 of the rat Acetyl CoA oxidase gene), and a DNA sequence encoding human CYP2A6 are shown in the Examples. In general, the cytochrome P450 catalysis system product is detected by illuminating the cell with light having a wavelength approximately equal to the excitation wavelength of the cytochrome P450 catalysis system product and detecting light at approximately the emission wavelength of the cytochrome P450 catalysis system product. When coumarin is used as the substrate for the cytochrome P450 catalysis system, the corresponding catalysis system product is 7-hydroxycoumarin, which has an excitation wavelength of about 368 nm and an emission wavelength of about 456 nm. The methods disclosed herein for measuring activation of receptors of the steroid hormone receptor superfamily (i.e., binding of these receptors to their specific ligands and subsequent promoter activation) do not require cell lysis or other labor-intensive manipulations and can be readily automated.

The above-described assay can be performed in a variety of mammalian host cells, provided that the cells express the receptor and include: (a) a reporter cassette for detecting formation of the receptor-ligand complex and (b) a cytochrome P450 catalysis system. The receptor cassette need not be contained on the same vector that contains the reporter cassette. However, it is essential that the DNA sequence containing each of these cassettes further includes a polyadenylation signal to permit successful transcription of the reporter (or receptor) gene into a functional mRNA (i.e., an mRNA which can be translated into a protein). A receptor cassette contained on a plasmid is optional if the host cell expresses the receptor natively. Thus, for example, the Examples illustrate a cytochrome P450 reporter gene assay for a receptor in which the glucocorticoid receptor is contained on the host cell chromosomal DNA.

The reporter (or receptor) cassette is delivered to the cell using routine transfection or transformation procedures (see, e.g., U.S. Pat. No. 5,429,948 issued to Crespi et al., for a description of a protoplast fusion procedure useful for delivering the reporter cassettes disclosed herein into mammalian cells). Electroporation to deliver the disclosed reporter cassettes to lymphoblastoid cells is described in the Examples.

Incorporation of the reporter (or receptor) cassette into a plasmid vector is optional and serves only to facilitate the construction of the reporter (or receptor) cassette, its transfection and selection. The cells could be transfected with naked reporter cassette DNA and laboriously screened for colonies containing reporter cassette DNA that had integrated into the host DNA and was functional.

In general, the vectors used to transfect AHH-1 cells in the Examples are derivatives of the plasmid pHebo described by Sugden et al., *Mol. Cell Biol.* 5:410-413 (1985). These vectors contain the bacterial origin of replication from pBR322 for replication in bacteria and the ampicillin resistance gene for selection of cells which have taken up the vector (note that bacterial genes do not contain intervening sequences and are equivalent to cDNAs). These vectors also contain the Epstein Barr Virus origin of replication which allows the vector to replicate as an extrachromosomal plasmid in cells which contain the EBV Nuclear Antigen 1 (essentially all human B lymphoblastoid cells). The vectors further contain a selectable marker (a bacterial gene) for use in the host (mammalian) cell conferring either Hygromycin B or 1-histidinol resistance. A derivative of pHebo exists which also contains EBNA-1 and will function in any human cell and most non-rodent mammalian cells. Incorporating the reporter (or receptor) cassette into a high copy number vector conferring resistance to 1-histidinol can be used to increase the overall expression levels of the reporter enzyme (or receptor) and thereby increase the amount (basal and induced) of cytochrome P450 catalysis system product produced in an assay.

It should be understood that various changes and modifications of the preferred embodiments may be made within the scope of this invention. For example, other human cell lines or mammalian cell lines may be used to receive the reporter cassettes of the invention. Likewise, the reporter cassettes of the invention can be used to measure the activity of a promoter sequence in methods other than those described herein. Thus, it is intended that all matter contained in the above description should be interpreted in an illustrative and not limiting sense.

All patents and other documents disclosed in this application are incorporated in their entirety herein by reference.

The Examples are followed by a Sequence Listing and what is claimed.

EXAMPLES

The Examples illustrate the feasibility of a cytochrome P450 reporter gene system for detecting receptor activation (Example I); optimization of the cytochrome P450 reporter gene system for detecting receptor activation (Examples II and III); and construction of utility vectors useful for practicing the invention (Example IV):

Example I

Optimization of the Cytochrome P450 Reporter Gene System for Detecting Receptor Activation A. Introduction.

We have demonstrated the feasibility of detecting chemicals which bind to the peroxisome proliferator receptor using a human cell line co-transfected with the peroxisome proliferator receptor (PPARα) and a novel reporter construct which responds specifically to activated PPARα. A cell line containing the mouse PPARα, a minimal Herpes simplex virus thymidine kinase (HSVtk) promoter coupled to the human cytochrome P4502A6 (CYP2A6) cDNA as a reporter and a peroxisome proliferator DNA responsive element (PPRE) exhibited a concentration dependent increase in CYP2A6-catalyzed coumarin 7-hydroxylase activity, upon treatment of the cells with clofibrate, ciprofibrate and WY14,463. The clofibrate-induced activity was 3 to 10 times higher than background levels in this cell line indicating an acceptable signal-to-noise ratio.

In a preferred embodiment, this system consists of a line of human B-lymphoblastoid cells which were transfected with extrachromosomal vectors containing the Ori P sequences derived from the Epstein Barr virus. These extrachromosomal vectors were used to introduce peroxisome proliferator receptors and reporter constructs which contain DNA elements responsive to the peroxisome proliferator receptor. The protocols for constructing the particular vectors for practicing the invention are described in Example IV.

In contrast to the work of Issemann, I. et al., *Nature* 347:645-650 (1990) which used a chimeric receptors and a transient transfection/expression system, we have used a human lymphoblast system which can be transfected to provide a stable transfection/expression system. The use of stable cell lines results in greater reproducibility and efficiency. Different vector constructs are available in the human lymphoblast system which can be maintained at high and low copy number. These allow the optimization of the response since different combinations of receptor and reporter elements in different copy number vectors are possible.

Two means of selection were used for the extrachromosomal vectors, resistance to hygromycin B which resulted in a vector copy number of approximately 5 per cell (pMF6- based vectors) and resistance to 1-histidinol which is a more stringent selection and resulted in a vector copy number of approximately 40 per cell (pEBVHistk-based vectors).

A novel aspect of the system is the reporter gene (CYP2A6). CYP2A6 catalyzes the 7-hydroxylation of coumarin which converts the non-fluorescent substrate, coumarin, to the highly fluorescent product, 7-hydroxycoumarin (umbelliferone). CYP2A6 is a low Km enzyme for this substrate and the Stokes shift for the product is very large with excitation at 368 nm and emission at 456 nm. The product is stable under physiological conditions and the assay can be performed directly on whole viable cells. Long incubation times at high cell concentrations yield linear product formation. This reporter system permits a one step flourometric detection of the reporter enzyme activity directly in a 96 well microtiter plate with no need for radioisotopes or chromatography. There is an excellent potential of automation with this system. Moreover, the cassettes, vectors and cell lines disclosed herein can be integrated into a kit format for routine testing of promoter activity and/or receptor activation.

B. Results.

The Results section is divided into two main subsections. The first, describes our studies with chimeric receptors containing the ligand binding region of PPARα coupled to the DNA binding region from the rat glucocorticoid receptor (GR). The reporter gene was coupled to a glucocorticoid responsive promoter (mouse mammary tumor virus long terminal repeat). The second subsection describes the use of native PPARα and the reporter genes coupled to promoters containing the peroxisome proliferator DNA responsive element (PPRE).

(1) Chimeric Receptors

Preliminary results provided some demonstration of the feasibility of this approach, but, also indicated significant need for improvements. In particular, we had developed vector constructs containing the mouse mammary tumor virus long terminal repeat (MMTV-LTR) coupled to the Rous Sarcoma virus (RSV) enhancer linked to the CYP2A6 cDNA. Also contained in this vector were PPARα/GR chimeric receptors. Treatment of these cells with clofibrate resulted in a very small but detectable, concentration-dependent increase in 7-hydroxycoumarin production by cell lines containing the chimeras. No increase was observed in control cells. However, expression from the MMTV-LTR was unstable, decreasing with a half life of approximately 5 days. Expression could be restored by growth of the cells is 5-azacytidine indicating that methylation was involved. In addition, the 7-hydroxycoumarin signal was too low to calculate an accurate signal-to-noise ratio.

We have performed a series of modifications to the promoter/enhancer in order to increase/stabilize expression. These studies utilized the native glucocorticoid receptor present in the host cells. In particular, an island of methylatable CpG sequences present between the TATA box and the cDNA were deleted (basepairs 1307 to 1554 of the pMAMneo sequence, Clontech, Palo Alto, Calif.). This resulted in a promoter with stable expression for greater than 60 days in continuous cell culture. The removal of the sequences did not appreciably affect the basal or dexamethasone-induced levels of reporter gene expression. Using the RSV enhancer, a maximal dexamethasone (DEX) induced coumarin 7-hydroxylase (CH) activity of 0.1 pmole per ($10^6$ cells×minute) was obtained, about 10 fold above basal levels.

We took two approaches to further enhance efficiency of expression. First, we identified an enhancer stronger than RSV and second, we moved the reporter construct from the low copy number vector to the high copy number vector. The data from testing a series of reporter constructs is contained in Example 1 Table 1. Cells were incubated for 2 days in 50 uM coumarin at an initial cell concentration of $1\times10^6$ cells per ml. DEX was added to a final concentration of 2.5 uM and TPA was added to a final concentration of 0.25 ug/ml. Product formation was measured fluorometrically at pH 9 with excitation at 368 nm and emission at 456 nm.

Potential enhancers including the Harvey Murine Sarcoma Virus (HaMSV), the u700 fragment of the mouse IgG heavy chain enhancer (Lenardo, M. et al., Nature 236:1573–1577 (1987)), an oligonucleotide containing a portion of the light chain, kappa, enhancer (SEQ. ID Nos. 3,4) and the SV40 early enhancer were tested individually and in combination. The u700 (constructs T147/T148) and SV40 (constructs T149/T150) enhancers were roughly comparable to the RSV enhancer while the HaMSV enhancer was 3 to 5 fold stronger than the RSV enhancer (construct T144). The use of multiple enhancers provided little improvement. In humans the $K_{E2}$ element is the compliment of the $K_{E1}$. Additional highly conserved regions of the mouse, rabbit and human Kappa enhancer (Emorine, L. et al., Nature 304:447–449 (1983)).

The T144 reporter construct was introduced into the high copy number vector (pEBVHistk) which confers resistance to 1-histidinol (construct designated pEHT144). The resulting cell line exhibited strong DEX-induced CH activity. The DEX inducibility was 7 to 10 fold and the maximal level of CH activity was 10–20 pmole/($10^6$ cells×min). The combination of the stronger enhancer and the higher vector copy number increased the the reporter gene signal relative to the initial construct (RSV enhancer, low copy vector) by about two orders of magnitude.

Cell lines containing the reporter gene on the vector conferring resistance to 1-hisitidinol (pEHT144) were then transfected with the chimeric receptors on the vector conferring resistance to hygromycin. Expression of the chimeric receptors was driven by the HSVtk promoter. Doubly transfected cells were selected on the basis of resistance to both hygromycin and 1-histidinol. Vectors without receptor (control) and containing chimeras with ligand binding regions from the mouse, rat and humans were transfected. Initial studies analyzing clofibrate induction of the reporter gene indicated a very high background activity from the reporter and a very poor signal-to-noise ratio (less than 10% increase in activity at 1.1 mM clofibrate). We examined whether the addition of lipopolysaccaride (LPS) and the co-incubation with the glucocorticoid antagonist, spironolactone, would improve this signal-to-noise ratio. We believed that the addition of LPS might induce transcription factors not normally present in the cells, but necessary for reporter function (Lenardo, M et al., Nature 236:1573–1577 (1987)) and that the addition of spironolactone would decrease background reporter expression by competing with endogenous ligand (hydrocortisone present in the serum supplement) for binding to the native GR. 0.2 ml cells were incubated in the wells of a microtiter plate for 2 days in 50 uM coumarin at an initial cell concentration of $1\times10^6$ cells per ml. Product formation was measured fluorometrically at pH 9 with excitation at 368 nm and emission at 456 nm. The addition of 5 ug/ml LPS and 10 uM spironolactone did improve the signal-to-noise ratio somewhat in cells containing the chimeric receptor. Cells containing the reporter alone did not respond to clofibrate induction of CH activity.

Cells containing chimeric receptors for the rat, mouse and human PPARα ligand binding domain and rat GR DNA binding domain, as well as control cells, were examined for CH induction by clofibrate in the presence of LPS and spironolactone during clofibrate treatment. Incubations contained 5 ug/ml E. coli lipopolysaccharide and 10 uM spironolactone and were uncorrected for cell progression. Incubations were performed under the same conditions as described above. No response was observed in control cells (containing vector without chimera). A 20–40% increase in CH activity was observed in cells with the rat, mouse and human chimeric receptors. The response induced by clofibrate was concentration-dependent with a maximum at 370 uM. The lower response at 1100 uM may be due to toxicity. Cells were grown in a volume of 0.2 ml in the wells of a 96 well microtiter plate from an initial cell density of $5 \times 10^5$ cells per ml. In the absence of clofibric acid, cells reached a final concentration of approximately $2 \times 10^6$ cells per ml. The T194, T194/T144 and T194/EH#7 cell lines contain the mouse PPARα cDNA. The AHH-1 TK± and T192/T144 cell lines do not contain the PPARα cDNA. Within the precision of this assay, there was no difference between the rat, mouse and human chimeras.

We have concluded that the use of chimeric PPARα/GR receptors does not appear to be a preferred approach at this time. This conclusion is based on the poor signal-to-noise ratio for clofibrate induction of the reporter. The high background in the assay is probably due to endogenous GR in the cell line which binds to an endogenous ligand and activates the reporter. An additional disadvantage of this approach is that the system will respond to both peroxisome proliferators and glucocorticoids since the cells contain a functional native GR. Although, the response to glucocorticoids can be controlled for by utilizing an appropriate control cell line, it is desirable to have a more specific assay. The addition of higher concentrations of the glucocorticoid antagonists is not a feasible approach because of the toxicity of these agents to the cells upon long term incubation. This toxicity can be reversed by the addition of dexamethasone (which induces the reporter). These observations imply that glucocorticoids and a functional GR are essential for the growth of AHH-1 TK± cells. It is also not feasible to increase the sensitivity of this assay by increasing expression of the chimeric receptors. Transfection of the HSVtk-driven (a stronger constitutive promoter than SV40 in this system) expression cassette for the chimeric receptors in the high copy number vector was lethal. Transfection of HSVtk driven expression cassettes for the native PPARα in the high copy number vector was not lethal. This suggests the possibility of an adverse interaction between the chimeric PPAR/GRs and the native GR (which is apparently required for cell growth).

An alternative approach would be development of chimeras based on the estrogen receptor. If the host cell lacks endogenous estrogen receptor, the signal-to-noise ratio may be acceptable and such a chimeric receptor may be better tolerated. We have also examined yet another approach which involved using a native PPARα coupled to a promoter containing a PPRE. This approach was more successful and our results are discussed in the next section.

(2). Native Receptor.

Recently, the DNA responsive element for the PPARα has been identified in the upstream noncoding regions of several genes known to be responsive to peroxisome proliferators. Tugwood, J. D. et al., EMBO Journal 11:433–439 (1992) have identified a PPRE associated with acyl CoA oxidase gene (ACO) and Muerhoff, A. S. et al., J. of Biol. Chem. 267:19051–19053 (1992) have identified a slightly different PPRE associated with the rabbit cytochrome P4504A6 gene (designated JCO in this Example). The sequences of the ACO and JCO elements are contained in SEQ. ID Nos. 5, 6 and 7.

We have coupled these responsive elements to minimal promoters and developed vectors containing the responsive element/promoter coupled to the CYP2A6 reporter and a PPARα which is expressed constitutively. For these studies, we have primarily used the PPARα from the mouse as a prototype. Extention to PPARα from the rat and human is accomplished, for example, by developing vectors containing the CYP2A6 reporter and using the PPARα from these species. Such methods involve substituting the analogous rat or human components for the mouse PPARα system components in the procedures described in detail herein.

As stated above, we utilized two responsive elements to develop the mouse PPARα system. The ACO PPRE is a fragment spanning –472 to –640 of the rat ACO gene. The JCO element is an oligonucleotide containing three repeats of the DNA binding domain from the rabbit CYP4A6 gene. These responsive elements were coupled to three different promoters. The first is a "minimal" HSVtk promoter derived from the vector pL 15CAT. This promoter spans a HgaI to BglII fragment of the HSVtk gene (157 bp, see U.S. Pat. No. 5,429,948, issued to Crespi et al. for a description of the plasmid pHEPtk1). This promoter is deficient only in the OCT sequence which is known to be important for constitutive expression from this promoter. We have also used a second HSVtk construct, designated #7, which contains a 121 bp EcoRI/BglII fragment with deletion of OCT and two other elements important for transcription, designated D2 and D3. The sequence of the HSVtK promoter region is shown in SEQ. ID No. 8.

Finally, we have used a derivative of the MMTV-LTR (SEQ. ID No. 9) which lacks the GREs and spans from basepairs 1168 (SacI site) to 1307 based on the numbering of the vector pMAMneo. This minimal promoter is contained on a DNA fragment of 130 bp and also has the methylatable CpG sequences between the TATA box and the reporter deleted.

We have used two enhancers with these minimal promoters. In both cases, the enhancer is contained in the PPARα expression cassette, which is in close proximity to the reporter construct in these vectors (due to the head to head orientation of the transcriptional cassettes). The PPARα is expressed using either the SV40 early promoter or HSVtk promoter (complete). Both of these promoters contain the OCT sequence.

The data in Example I Table 2 provide the results for the different vector constructs and the CH activity observed under basal conditions and after treatment with 1.1 mM clofibrate. MMTV-LTR1 is native, MMTV-LTR2 is minus CpG, MMTV-LTR3 is TATA only. Orientation is relative to reporter. CH activity is pmole per $10^6$ cell min. Assuming the cells double every 24 hours, the maximum cell density is $2 \times 10^6$ cells per ml, using the log average cell concentration for each day of exposure. Earliest post fusion-values were used. The inducing concentration of clofibrate used in Example I Table 2 is not the optimal concentration (i.e. highest response). It is merely a concentration in the monotonic portion of the dose response curve which has been used consistently in many experiments. A higher signal-to-noise ratio is observed at 3.3 mM clofibrate. This table contains results for control vector constructs (without PPARα) and constructs containing primarily the mouse PPARα.

Several conclusions can be drawn from these data:

1) The JCO appears to be ineffective in the system while the ACO appears to be quite effective. Coupling the JCO with either HSVtk/L15 or HSVtk/#7 results in little or no significant increase in CH activity following clofibrate treatment. In contrast, coupling the ACO to either HSVtk/L15, HSVtk/#7 or the MMTV-LTR promoters results in significant induction of CH upon clofibrate treatment.

2) The HSVtk/L15 promoter has a very high background and while induction can be observed over this background, the fold induction is limited (T194 construct). This high background is probably due to the fact that this promoter is deficient only in the OCT sequences and this function is being substantially restored by the promoter/enhancer driving the PPARα. The influence of having OCT in proximity to the PPRE is illustrated by the pairs of 7.3/T225 and 7.10/T225 constructs which differ in the orientation of the PPARα expression unit relative to the reporter. When OCT is close to the PPRE (head-to-head orientation of receptor and reporter), the basal expression from the HSVtk/#7 promoter is about 10 fold higher than when OCT is distant from the PPRE (head-to-head orientation).

Comparing the two HSVtk promoters, HSVtk/L 15 and HSVtk/#7, shows that the latter promoter has a much lower background and only a slightly lower clofibrate-induced response, the combination of which gives a substantial improvement in signal-to-noise ratio relative to HSVtk/L15. A comparison of the response for the "L15" promoter (T194) and the "#7" promoter (T194/HSVtk/#7), normalized to their respective basal levels, indicated a substantial improvement in signal-to-noise ratio. The comparison was performed by incubating 0.2 ml cells for 3 days in the wells of a microtiter plate at an initial cell concentration of 5×10$^5$ cells per ml in the presence of increasing amounts of inducer and 50 uM coumarin. Product formation was measured fluorometrically at pH 9 with excitation at 368 nm and emission at 456 nm. The reporter is not induced in cells which do not contain a PPARα indicating that little endogenous PPARα is present in AHH-1 TK± and that appropriate control cell lines can be developed.

Production of 7-hydroxycoumarin as a function of clofibrate concentration also was compared between T194 (HSVtk/L15 promoter) and T194/T144 which contains the minimal MMTV-LTR promoter both with the ACO PPRE, as well as with a control construct (T192/T144) which has the MMTV-LTR promoter and the ACO PPRE but does not contain the PPARα. The above-described assay conditions were used and the results were normalized to the respective basal expression levels. In the absence of the PPARα, no induction was observed. Addition of the PPARα expression cassette raised the basal CH activity. The basal levels of expression were quite different for T194 and T194/T144. However, the signal-to-noise ratio was similar indicating that the use of the minimal MMTV-LTR promoter did not offer an advantage.

Since the T194/HSVtk/#7 construct gave the best signal-to-noise ratio, we have examined other aspects of the response. Concentration response data were obtained using the T194/HSVtk/#7 construct for three peroxisome proliferators, WY14,463, ciprofibrate and clofibrate. All three agents induced concentration-dependent increases in reporter gene expression. On a molar basis, WY14,463 is the most potent followed by ciprofibrate and then clofibrate. These differences in potency are similar to that observed in vivo.

The reporter gene expression as reported in previous tables and figures is expressed as pmoles product/well in a 96 well microtiter plate as measured fluorometrically. Such measurements do not correct for the effects of toxicity or cell progression which occur during treatment. A toxicity curve reflecting the relative number of cells/well present at the end of treatment was obtained as a function of chemical concentration. Both clofibrate and ciprofibrate are toxic to the cells with ciprofibrate being more toxic on a molar basis. The CH activity observed at high chemical concentrations is likely suppressed due to toxicity. This suppression was observed as a decline in basal CH activity in the control construct T192/T144. This suppression can be corrected for by determining the cell concentration in the well or by determining the suppression of CH activity in a cell line which constitutively expresses the reporter.

Concentration response data for reporter gene expression induced by clofibrate and ciprofibrate also were obtained and the data was graphed as pmole/well and pmole/million cells. The data indicated that the response per cell in the well is substantially greater than gross fluorescence/well. A signal-to-noise ratio of about 10 was observed for both agents upon correction for cell number.

In order to determine whether differential survival affects the response control cells versus cells bearing a PPARα, we have examined the toxicity of clofibrate and ciprofibrate in untransfected cells, cells with the reporter without PPARα and cells containing three different reporter/PPARα constructs. No differences in toxicity was observed among any of the cell lines. Therefore, the expression of the reporter does not confer differential toxic effects.

TABLE I

EXAMPLE I
REPORTER CONSTRUCTIONS

| Cell Line Designation | Plasmid | Enhancer 1 | Enhancer 2 | Responsive Element | Promoter | Coumarin Hydroxylase Activity | | |
|---|---|---|---|---|---|---|---|---|
| | | | | | | Basal | DEX Induced | DEX/TPA Induced |
| T144 | pMF6 | HaMSV | NONE | GRE | MMTV-LTR2 | 0.05 | 0.3–0.5 | 0.6–0.9 |
| pEHT144 | pEBVHIStK | HaMSV | NONE | GRE | MMTV-LTR2 | 1.4 | 14.4 | 20.6 |
| T147 | pMF6 | u700 | NONE | GRE | MMTV-LTR2 | 0.03 | 0.23 | 0.35 |
| T148 | pMF6 | u700 | NONE | GRE | MMTV-LTR2 | 0.02 | 0.15 | 0.25 |
| T149 | pMF6 | SV40 | NONE | GRE | MMTV-LTR2 | 0.07 | 0.18 | 0.22 |
| T150 | pMF6 | SV40 | NONE | GRE | MMTV-LTR2 | 0.06 | 0.16 | 0.20 |
| T153–T155 | pMF6 | SV40 | u700 | GRE | MMTV-LTR2 | ND | ND | ND |
| T156 | pMF6 | MSV(5'-3') | SV40 | GRE | MMTV-LTR2 | 0.020 | 0.097 | 0.27 |
| T157 | pMF6 | MSV(5'-3') | SV40 | GRE | MMTV-LTR2 | 0.017 | 0.097 | 0.20 |
| T162 | pMF6 | u700(3'-5') | SV40 | GRE | MMTV-LTR2 | 0.013 | 0.042 | 0.075 |

TABLE I-continued

EXAMPLE I
REPORTER CONSTRUCTIONS

| Cell Line Designation | Plasmid | Enhancer 1 | Enhancer 2 | Responsive Element | Promoter | Coumarin Hydroxylase Activity | | DEX/TPA Induced |
|---|---|---|---|---|---|---|---|---|
| | | | | | | Basal | DEX Induced | |
| T163 | pMF6 | u700(3'-5') | SV40 | GRE | MMTV-LTR2 | 0.017 | 0.056 | 0.12 |
| T168 | pMF6 | RSV | SV40 | GRE | MMTV-LTR2 | 0.014 | 0.068 | ND |
| T169 | pMF6 | RSV | SV40 | GRE | MMTV-LTR2 | 0.025 | 0.14 | ND |
| T174 | pMF6 | KAPPA | NONE | GRE | MMTV-LTR2 | 0.004 | 0.004 | |
| T176 | pMF6 | HaMSV(5'-3') | KAPPA | GRE | MMTV-LTR2 | 0.04 | 0.3–0.5 | 0.7 |
| T177 | pMF6 | HaMSV(5'-3') | KAPPA | GRE | MMTV-LTR2 | 0.046 | 0.26 (Unstable) | 0.58 |
| T178 | pMF6 | HaMSV(3'-5') | KAPPA | GRE | MMTV-LTR2 | 0.045 | 0.34(Inducibility lost) | 0.46 |
| T180 | pMF6 | RSV | KAPPA | GRE | MMTV-LTR2 | 0.02 | 0.07 | nd |

TABLE 2

EXAMPLE I
NATIVE PPAR CONSTRUCTIONS

| Cell Line Designation | Receptor | | | Reporter | | | Coumarin Hydroxylase Activity | |
|---|---|---|---|---|---|---|---|---|
| | Promoter | Orientation | Type | Enhancer | Responsive Element | Promoter | Basal | Induced (Fold) |
| T192 | NA | NA | NONE | HSVtk-OCT | ACO | HSVtkL15 | 0.37 | 0.30(0.8) |
| T194 | SV40 | 3'-5' | mPPAR | HSVtk-OCT | ACO | HSVtkL15 | 0.19 | 0.29(1.5) |
| T245 | NA | NA | NONE | HSVtk-OCT | JCO | HSVtkL15 | 0.25 | 0.23(0.9) |
| T247 | HSVtk | 3'-5' | mPPAR | HSVtk-OCT | JCO | HSVtkL15 | 0.52 | 0.60(1.2) |
| T248 | HSVtk | 3'-5' | hPPAR | HSVtk-OCT | JCO | HSVtkL15 | 0.34 | 0.32(0.9) |
| T249 | HSVtk | 3'-5' | hPPAR | HSVtk-OCT | JCO | HSVtkL15 | 0.37 | 0.41(1.1) |
| T192/T144 | NA | NA | NONE | HSVtk-OCT | ACO | MMTV-LTR3 | 0.025 | 0.018(0.7) |
| T194/T144 | SV40 | 3'-5' | mPPAR | SV40 | ACO | MMTV-LTR3 | 0.064 | 0.076(1.2) |
| T194/HSVtk#7 | SV40 | 3'-5' | mPPAR | SV40 | ACO | HSVtk#7 | 0.018 | 0.059(3.3) |
| 7.3/T225 | HSVtk | 3'-5' | mPPAR | SV40 | JCO | HSVtk#7 | 0.020 | 0.0.18(0.9) |
| 7.3/T225 | HSVtk | 5'-3' | mPPAR | SV40 | JCO | HSVtk#7 | 0.002 | 0.003(1.5) |
| 7.10/T225 | HSVtk | 3'-5' | mPPAR | SV40 | JCO | HSVtk#7 | 0.014 | 0.012(0.9) |
| 7.10/T225 | HSVtk | 5'-3' | mPPAR | SV40 | JCO | HSVtk#7 | 0.002 | 0.000(0.0) |
| T194/T144/JCO | SV40 | 3'-5' | mPPAR | SV40 | JCO | MMTV-LTR3 | ND | |

Example II

Optimization of the Cytochrome P450 Reporter Gene System for detecting Receptor Activation A. Introduction.

(1) Confirmation of Results of Example I.

In Example I, we demonstrated that cells bearing a vector construct containing the mouse PPARα (expressed with an SV40 early promoter), a PPRE derived from the acyl CoA oxidase gene regulatory sequences and either a minimal herpes simplex virus thymidine kinase (HSVtk) promoter or a minimal mouse mammary virus long terminal repeat (MMTV-LTR) promoter coupled to the CYP2A6 cDNA demonstrated a concentration dependent increase in the CYP2A6 catalyzed coumarin 7-hydroxylase activity upon treatment with clofibric. The vector construct with the HSVtk and MMTV-LTR promoters were designated T194EH#7 and T194/T144 respectively. Control constructs, without the PPARα (designated T192/T144) and with constitutive CYP2A6 expression (p91Dtk) were also examined.

In this test we used an initial cell concentration of 2 million cells/ml contained in 0.2 ml culture medium per well of a 96 well microtiter plate. Coumarin (0.05 mM) and clofibrate (concentration was an experimental variable) were added at the beginning of the incubation time. Cells were incubated for 3 days and the 7-hydroxycoumarin content in the wells was analyzed by fluorescence with excitation at 360 nm and emission at 460 nm using a Cytofluor 2350 (Millipore). We observed an improvement in 7-hydroxycoumarin fluorescence by the addition of 0.1 ml of Tris pH9 prior to analysis of the fluorescence. The elevation in pH increases 7-hydroxycoumarin fluorescence by increasing the proportion of the fluorochrome which is ionized. Quantitation was achieved by comparison to a 7-hydroxycoumarin standard curve. A clofibrate concentration-dependent increase in 7-hydroxycoumarin levels was observed in cells bearing T194EH#7. No significant induction was observed in cells bearing T192/T144.

(2) Verification of the Response of the Cytofluor 2350

A Cytofluor 2350 fluorescent plate scanner was used for the primary data acquisition for 7-hydroxycoumarin concentrations in the wells of the 96 well plate. An entire plate can be scanned in 1 to 2 minutes and the data becomes available in a computer compatible format which allows facile data reduction/analysis.

The response of the Cytofluor is linear over a substantial 7-hydroxycoumarin concentration range (0–1250 pmoles). In addition, the elevation of the pH in the wells of the plate by the addition of 0.1 ml 0.1M Tris pH 9 substantially increased the fluorescent signal from the 7-hydroxycoumarin without affecting the background. This effect is likely due to the shift in 7-hydroxycoumarin to the more fluorescent, ionized form at higher pH. Elevation of the pH through the addition of the Tris pH 9 has been adopted for routine analyses.

(3) Construction and Test of the Reporter with PPREs

It has been reported that the incorporation of multiple PPREs can improve the signal to noise ratio in transient expression systems using PPARα/PPRE. We evaluated whether the introduction of multiple PPREs would improve the responsiveness in this system. To accomplish this evaluation, a PPRE sequence was isolated and introduced into a vector already containing the PPARα and a single PPRE.

We have isolated the Acyl CoA Oxidase Peroxisome Proliferative Responsive Element (ACO-PPRE) with Kpn I ends by Polymerase Chain Reaction (PCR) using a vector construct containing the ACO PPRE as substrate (the T194 vector described in Example I). The PCR product was then digested with Kpn I to generate cohesive ends and introduced to a vector containing the mouse PPARα and a single ACO-PPRE (T194EH#7).

First, a Kpn I partial digest, which cuts between the existing ACO-PPRE plus minimal promoter HSVtk#7 and the mouse PPARα was performed in the vector T194EH#7. The vector was treated with calf intestine phosphatase to prevent religation of the vector to itself. The ACO-PPRE-PCR was ligated into the Kpn I site next to the minimal promoter HSVtk#7. The ACO-PPRE was present in molar excess to facilitate the incorporation of multiple inserts. The ligation products were introduced into bacteria and the position of the ACO-PPRE insert was verified by restriction mapping. The clones, numbered ACO#14, ACO#19 and ACO#43, were identified as having two ACO-PPRE units.

In order to introduce additional ACO-PPRE units, a second round of partial digest/ACO-PPRE insertion was performed. A Kpn I partial digest of ACO#43 was performed, and the ACO-PPRE-PCR fragment was ligated into the vector. The position and number of ACO PPREs inserts were verified by restriction mapping. Two clones, numbered ACO²#16 and ACO²#19, had three ACO-PPRE copies per construct.

The responsiveness of the reporter constructs was evaluated in AHH-1 TK± cells. AHH-1 TK± cells were transfected via protoplast fusion with vectors containing the single, double and triple copies of ACO-PPRE. Alternatively, cells can be transfected with the vectors using electroporation. Cells bearing the vector were selected via resistance to hygromycin B. The responsiveness of the different ACO-PPRE constructs was examined using clofibrate as a model compound.

Methods For Clofibrate Induction Assays.

The ACO-PPRE constructs were centrifuged and resuspended at a density of 2 million cells per milliliter in RPMI media with 9% horse serum. One hundred microliters of the cell suspension was distributed into a total of four rows, two rows being at the opposite end of a 96 well microtiter plate. One set was labeled as clofibrate and the other set was labeled as the blank. Clofibrate was then added at concentration of 3 mM, 2 mM, 1 mM, 0.5 mM & 0 mM to the appropriate wells. Stock concentration of clofibrate was 50 mM in 75 mM NaOH. One hundred microliters of media containing 100 micromolar coumarin was then added to the clofibrate containing wells. The negative control contained cell suspension and 100 uM coumarin only. The plates were placed at 370 Celsius for three days. In a distinct set of wells, one hundred microliters of hydroxy-coumarin standard was placed in two rows The concentrations are in units of pmoles and the values are: 1250, 625, 313, 156, 78, 39, 19.5 & 0. At the end of the three day incubation period, one hundred microliters of media containing 100 uM coumarin was added to the wells labeled as blank. Next 0.1M Tris pH 9.0 was distributed to the contents of each well. Fluorescence was analyzed with a cytofluor 2350 (Millipore) with excitation at 360 nm and emission at 460 nm (both filters with a 40 nm bandwidth). The net fluorence was calculated by subtracting the fluorescence of the blank wells from the fluorescence of the test wells for each clofibrate concentration. Conversion to pmole product per well was accomplished by comparison to the fluorescence of the standards. The responsiveness of the different constructs to clofibrate induction was measured immediately after viable, hygromycin resistant cells were obtained and periodically thereafter in order to evaluate the stability of the system. The data were graphed as the fold induction relative to the without clofibrate control incubation. This is a measure of the responsiveness of the system and corrects for differences in the negative control values for the different reporter constructs. The number of ACO PPREs in the reporter construct ranged from 1 to 3: "1×" is T194EH#7, "2×" is ACO#43 and "3×" are ACO² #16 or #19. The other "2×" constructs (ACO#14 and ACO#19) were also evaluated in an independent experiment and were found to respond similarly to ACO#43. ACO#43 was arbitrarily chosen for subsequent constructions/analyses because it appeared to have a slightly better signal to noise ratio than ACO#14 or ACO#19.

The results showed the responsiveness in clofibrate induction of CYP2A6 catalyzed coumarin 7-hydroxylase activity in cells transfected with reporter constructs with different numbers of PPREs. Two independent assays (different days) were performed on the same transfected populations immediately after the cells became hygromycin resistant. Maximum response appears (as fold increase) in parenthesis: At 15 days after transfection, 1×(2.6), 2×(2.8), 3×(4.1 or 3.9); at 19 days after transfection, 1×(3.6), 2×(5.6), 3×(6.1 or 4.5).

The cells bearing the vectors with multiple PPREs responded more strongly to the clofibrate inducer than the cells with the single PPRE construct. It appears that three PPREs are better than 2 PPREs which is in turn better than 1 PPRE. Interestingly, much of the improvement in the signal to noise ratio is due to a reduction in the background fluorescence in the wells without clofibrate.

We have begun to examine the stability of the inducibility and background (control) 7-hydroxycoumarin production as a function of growth in cell culture. For this analysis only the cells transfected with "1×" and "3×" PPREs were carried through the experiment. The "2×" had a responsiveness which was intermediate to these constructs and was not analyzed further. These additional assays were performed at 23, 26, and 54 days after transfection.

The results of these additional assays suggest that the responsiveness of the system decreased as a function of time of growth in exponential cell culture. The fold induction decreases in a time-dependent manner from about 4 to 6 fold to about 2 fold. The level of 7-hydroxycoumarin production in the negative control wells appears to be unchanged. Very similar responses were obtained in assays by two different individuals when the two independent assays were performed on the same day. In all assays, the "3×" construct was more responsive than the "1" construct. We utilized the "3x" PPRE construct for the next round of development of the reporter construct.

We examined whether the apparent instability is due to methylation at CpG sequences through analyses with and without the addition of deoxy-5-azacytidine (5dAC) to the cell cultures. Addition of 0.25 ug/ml 5dAC increased the clofibrate induced signal 20 to 50 fold. This suggests that methylation is responsible for the loss of responsiveness. This experiment did not determine whether the loss of responsiveness was due to loss of receptor transcription or loss of reporter function.

We also examined whether the reduction in responsiveness is due to effects on the reporter expression unit or whether it is due to a decrease in expression of the PPARα. We have previously observed CYP2A6 expression from the HSVtk promoter to be stable for many months in cell culture. However, it is possible that the lower transcription level present with the minimal promoter permits more rapid methylation. These experiments are described in the next section.

(4) Construction and Application of the Versatile Vector

In the previous section we examined the effect of multiple PPREs on the responsiveness of a CYP2A6-containing reporter construct to clofibrate treatment. The results of these experiments indicated that multiple PPREs are beneficial for increasing signal to noise ratio. We also plan to examine whether alternative promoters for the PPARα will improve the responsiveness of the system and whether the introduction of enhancers will also improve responsiveness. Given the multiplicity of different reporter constructs to be examined, it is beneficial to have a versatile vector with a polylinker containing many unique restriction sites in order to easily prepare these constructs. Therefore we have modified an existing "utility" vector in order to make it more versatile.

We started with the "utility" vector which was developed in our laboratory and designated p91DtkEH#7. This vector is based on pMF6 containing CYP2A6 cDNA. A fragment from the Hind III site in the vector to the Eco RI site in the HSVtk promoter for the CYP2A6 cDNA was deleted and the polylinker from pUC19 (Hind III to Eco RI) was inserted. This vector contains the minimal HSVtk promoter which was used successfully in Example I. However, due to other sites in the vector, many of the restriction sites in the pUC 19 polylinker are no longer unique. These include, Eco RI, Sac I, Sma I, Bam HI, Pst I and Sph I. Only Kpn I, Xba I, Sal I and Hind III are unique. However, some of these sites are of limited usefulness because the PPARα has a Kpn I site and the expression units used for PPARα expression (SV40 or HSVtk) contain Hind III, Sal I and Xba I sites for cDNA insertion. Therefore the polylinker was removed and a new polylinker was inserted.

Modification of the vector p91DtkEH #7 began with a restriction enzyme digest at the Hind III & Kpn I sites. The objective was to replace the polylinker with one derived from an oligonucleotide having sites at Hind III, Cla I, Avr II, Bgl II, Nhe I, Not I and Kpn I sites. Complimentary oligonucleotides (see Example IV) were prepared, kinased and ligated into the Hind III/Kpn I digested vector. The resulting plasmid containing the polylinker was designated p2A6pl. The structure of p2A6pl was confirmed by restriction digests.

We then proceeded to introduce SV40 early- and HSVtk-derived expression units (including a polyadenylation signal sequence) into p2A6pl in order to provide a means for PPARα expression. During the course of this construction we discovered some unexpected modifications (duplications) in the polylinker in p2A6pl which were corrected.

To introduce the SV40 early promoter, it was also necessary to modify the polylinker contained in the commercially available vector in order to have unique restriction sites for the introduction of cDNAs. Modification of cloning vector T275, a pSG5 derivative modified to give the capability of excising the SV40 expression unit with Cla I in addition to Sal I, began with removal of the polylinker with the restriction enzymes Eco R I and Bgl II. The polylinker was replaced with an oligonucleotide containing sites for Xba I, Xho I and Hind III (see Example IV). The Eco RI site was restored and the Bgl II site was lost upon introduction of the new polylinker. The configuration of the polylinker was verified by restriction mapping. The desired construct was designated T275pl1.

The HSVtk (high expression, not a minimal promoter) expression unit (promoter sequence) was derived from an existing plasmid (pHyHopl4) which contained a short polylinker containing Hind III, Bam HI, Xba I and Sal I sites for cDNA insertion. The entire expression unit can be excised with Nar I.

The next step was to introduce the SV40 early and HSVtk expression units into p2A6pl. The SV40 early expression unit was excised from T275pl1 with Cla I (a 1.2 kb fragment). The HSVtk expression unit was excised from pHyHop14 with Nar I (a 1 kb fragment). These fragments were ligated into p2A6pl which had been digested with Cla I and treated with calf intestine phosphatase (Nar I and Cla I have the same cohesive ends).

The ligation products were introduced into bacteria and individual clones were screened for the presence of the insert and then orientation of the insert. Two orientations are possible (symmetrical cohesive ends on the insert and vector) and we examined both orientations as orientation of the expression unit and its endogenous enhancers may affect background expression level from the CYP2A6 reporter unit, and also potentially, the responsiveness of the reporter.

Figure 2:
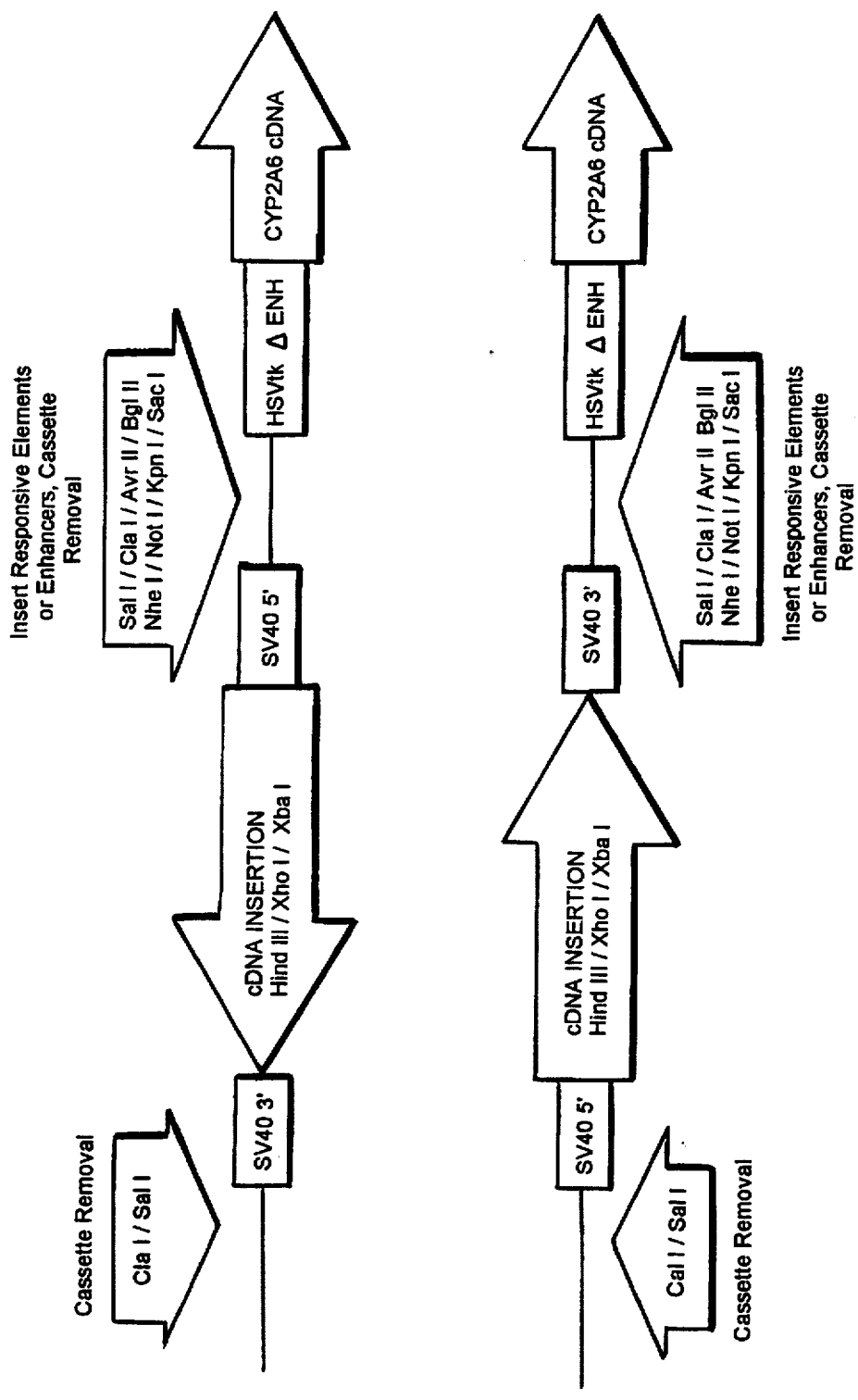
FIG. 2. Schematic diagrams of the cDNA insertion and reporter portions of p2A6p1SV derivatives. The remaining portion of the plasmid contains the OriP sequences, the genes conferring resistance to hygromycin B and ampicillin. Upper diagram is isolate "296" lower diagram is isolate "2838". These two isolates differ only in the orientation of the HSVtk expression unit.

The resulting plasmids containing the HSVtk promoter for PPARα cDNA insertion were designated p2A6plTK414 and p2A6plTK1212. These two constructs differ only in the orientation of the HSVtk expression unit and are diagrammed in FIG. 1. The resulting plasmids containing the SV40 early promoter for PPARα cDNA insertion were designated p2A6plSV2838 and p2A6plSV296. These two constructs differ only in the orientation of the SV40 early expression unit and are diagrammed in FIG. 2.

We introduced the mouse PPARα into all four of the vector constructs along with the "3x" ACO PPRE (the most responsive element as identified in the previous section). We then transfected the cells and analyzed the background reporter expression level and responsiveness to clofibrate induction for these "complete" reporter constructs. The SV296 construction gave the best response (this is analogous to the previous "3x" ACO constructs). As in the previous experiments, responsiveness appeared to decrease with time.

We verified the functionality of the HSVtk and SV40 early expression units by the introduction of a cDNA encoding an easily assayed enzyme. We used CYP2D6 which catalyzes bufuralol 1'-hydroxylase activity. This assay is sensitive and specific. The CYP2D6 cDNA was introduced into the Xba I site and the orientation verified by restriction mapping. Cells were transfected and hygromycin B resistant cells selected. Bufuralol 1'-hydroxylase activity was assayed in the transfected cells. All constructs were active with essentially the same level of expression.

We examined the stability of bufuralol 1'-hydroxylase activity (CYP2D6 expression) in the SV296 based construction as a means to better understand the apparent instability of the responsiveness of the reporter constructs analyzed in the previous section (e.g., to determine whether the apparent instability was due to a decrease in expression from the promoter used to express the PPARα). Because we did not have available the means to examine the expression of PPARα protein directly (e.g., using an immunoassay with antibodies specific for the PPARα protein), we used the CYP2D6 cDNA as a PPARα "surrogate". There is a sensitive catalytic assay for this protein (bufuralol 1'-hydroxylase) and this assay can be performed simultaneously with the coumarin 7-hydroxylase assay. We simultaneously determined the level of background expression for the CYP2A6 reporter gene.

The expression of CYP2D6 (measured as bufuralol hydroxylase activity) from the SV40 expression cassette (used to express the PPARα in the SV296 based constructions) was stable during growth in culture and the expression level was not affected by treatment with 5dAC. In contrast, the basal expression of CYP2A6 (measured as coumarin hydoxylase activity) from the truncated HSVtk expression cassette (the reporter construction) declined with time in culture and activity could be restored by treatment with 5dAC. This indicates that the loss of responsiveness observed in the previous experiments is due to methylation in the reporter cassette and not in the receptor expression cassette.

(5) Construction and test of reporters with the HaMSV enhancer

We investigated the use of alternate enhancer elements by inserting the HaMSV enhancer into the Nhe I site in the four 3× PPRE constructs of Example II. Both orientations of the enhancer were obtained. One construction based on p2A6pITK isolate 414 gave greater than a 12 fold induction with clofibrate treatment. This is a sufficient signal to noise ratio to practice the invention. As many of the CpG sequences as possible will be removed from the PPRE/HSVtk region to further increase stability (presumably, by reducing the likelihood of methylation-induced instability. Alternatively, stability can be increased by constructing an analogous construction utilizing the MMTVLTR/PPRE (described in Example III). We have found that the responsiveness from the native MMTVLTR (glucocorticoid responsive element) is stable when the HaMSV enhancer is used.

(6) Test of the High Copy Number Reporter

One of the observations in Example I was that the overall signal (background and clofibrate induced) was relatively low. This necessitated relatively long incubations (several days). Therefore, in addition to the efforts described above to increase the signal to noise ratio (or responsiveness) of the system, we have examined a means to increase the overall signal of the system.

The approach was to utilize both the high copy number vector and the low copy number vector to reconfigure the system. All of the work describe above used the low copy number vector conferring resistance to hygromycin B. We also have available to the program a high copy number vector conferring resistance to 1-histidinol (HisD gene). We produced vector constructs which contained the PPRE (ACO)/CYP2A6 construct in a vector conferring resistance to 1-histidinol and the mouse PPARα in a vector conferring resistance to hygromycin B. (Note: the latter vector also had a PPRE/CYP2A6 reporter of the same type but the influence of this reporter is expected to be minor due to its low copy number.)

The high copy number reporter construct was prepared by excising the entire CYP2A6 reporter/promoter/PPRE (ACO)/SV40 promoter (enhancer) unit from either T194EH#7 or T194/144 with Hind III and Spe I (a portion of the OriP sequences was also contained in this fragment). This fragment contained the entire SV40 early promoter used originally for PPARα expression and a few bases of the PPARα cDNA. The SV40 sequences were included because we believe that the SV40 enhancer is important for reporter function.

The reporter construct was introduced into two different vectors digested with the same enzymes. The first was pEBVHis, which confers resistance to 1-histidinol but has no cDNA expression-related sequences. We were concerned about the degree of function of the HisD gene because the SV40 promoter reads directly into the HSVtk promoter used to expressed the HisD gene. There was the possibility of poor HisD gene expression due to promoter interference. Therefore we prepared a parallel set of constructs based on digestion of pH44 (pEBVHis derived but containing CYP3A4 expression units) digested with the same enzymes. With these latter constructions the Hind III site is in the CYP3A4 cDNA immediately prior to the Poly A signal which would provide a terminator of transcription from the SV40 promoter and hence eliminate any promoter interference with the HisD gene (Crespi et al., Carcinogenesis 12:335-359 (1991)).

The vectors were introduced in two steps: first the high copy number vector was introduced and bulk 1-histidinol resistant cells were selected. No 1-histidinol resistant cells were obtained for the pEBVHis-derived plasmids while 1-histidinol resistant cells were obtained for the pH44-derived plasmids. It appears that our concern about promoter interference was well founded.

The bulk 1-histidinol resistant cells bearing pH44-derived plasmids were then transfected with the constructs bearing the PPARα (T194EH#7 or T144/194) and bulk and clonal hygromycin resistant/1-histidinol resistant cells were selected. The clonal derivatives were isolated by colony formation in microtiter plates. Coumarin was added to the plating media so cells with a functional reporter unit could be identified by the presence of 7-hydroxycoumarin fluorescence.

The colonies for T144/194 appeared to be fewer, smaller and with less 7-hydroxycoumarin fluorescence than the colonies for T194EH#7. Four and sixteen 7-hydroxycoumarin positive colonies were isolated bearing T144/194 and T194EH#7 respectively. These clonal isolates were propagated to bulk, clonal-derived cultures.

Clofibrate-induced CYP2A6 activity was assayed in the bulk-selected and clonal populations. The same methods described previously were used. Surprisingly, the bulk-selected cells had a very low background (17 pmole and 8 pmole per well for T144/194 and T194EH#7 respectively) and no clear induction of CYP2A6 was observed (less than 1.5 fold).

For the clonal populations, three of the T144/194-derived clones and seven of the T194EH#7-derived clones grew up to bulk cultures. Clofibrate-induced CYP2A6 activity was assayed in the clones. The results are contained in the Table below. (Note: the values separated by commas are for sequential independent determinations.)

| Vector | Clone Designation | Background (pmole) | Maximum Fold Induction |
|---|---|---|---|
| T144/194 | 6-1 | 318, 236, 190 | 1.57, 1.5, 1.65 |
| " | 6-3 | 237, 448 | 1.17, 1.3 |
| " | 6-4 | 355 | 1.36 |
| T194EH#7 | 8-1 | 1100 | 1.04 |
| " | 8-5 | 1327, 1760, 1550 | 1.27, 1.24, 1.3 |
| " | 8-6 | 5 | 3.44 |
| " | 8-11 | 1560 | 1.15 |
| " | 8-12 | 1490 | 1.21 |
| " | 8-14 | 1250 | 1.15 |
| " | 8-16 | 23 | 3.73 |

Several conclusions can be reached from these data. First, clones 8-6 and 8-16 probably did not contain functional high copy number reporter. The background values and the fold induction are consistent with only the low copy number vector being present. However, transfection with a low copy number vector with only the PPARα would clarify this interpretation. Second, T194EH#7 has a higher background than T144/194. This is consistent with the relative backgrounds with the low copy number vector. Third, background for the active clones is much higher than expected based on the 8 fold difference in vector copy number for hygromycin B-resistance versus 1-histidinol resistance. We would have expected 8×20 pmole or 160 pmole for T194EH#7 and we observed approximately 10 fold higher. Fourth, the signal to noise ratio has been substantially decreased to barely significant levels.

Example III

Further Optimization of the Cytochrome P450 Reporter Gene System of Example II

A. Introduction.

(1). Stability of expression of the HSVtk based reporters

We produced a series of constructs containing (from 5' to 3') as a reporter: the MSV enhancer, three copies of the ACO PPRE, a truncated HSVtk promoter, the CYP2A6 cDNA and a polyadenylation signal sequence.

A mouse PPARα expression cassette was located 5' of the reporter. The PPARα expression cassettes were driven by the SV40 or HSVtk promoters. Both orientations of the PPARα cassette relative to the reporter were produced. One of these, TKdENH/MSV 296 #53, with the PPARα expressed from the SV40 promoter and head to head orientation gave a greater than 10 fold increase in CYP2A6 expression after exposure to clofibrate.

We monitored the stability of clofibrate induced expression as a function of time in culture. The basal activity and induced activity declined to near zero with time in culture. For comparison, these results were compared with the data from the T194/T144 construction. This construction contained one copy of the ACO PPRE, a truncated MMTV LTR promoter/TATA box (the sequences downstream from the glucoconicoid responsive element) and cDhe CYP2A6 cDNA. The mouse PPARα is expressed from the SV40 promoter with head to head orientation. There was initially some decline in both basal activity and induced activity. However, the fold inducibility remained fairly constant although lower than the initial value for TKdENH/MSV 296 #53.

We had been successful in developing a 10 fold-inducible OR expression cassette for our cell lines which constitutively express human P450's by using the entire glucocorticoid responsive MMTV LTR (the parent cell line expresses a functional glucocorticoid receptor) and the MSV enhancer. This suggested that a fruitful construct might employ the MSV enhancer, multiple PPRE's and the truncated MMTV LTR promoter/TATA box.

(2). Construction of the MMTV LTR based reporters

Figure 3:
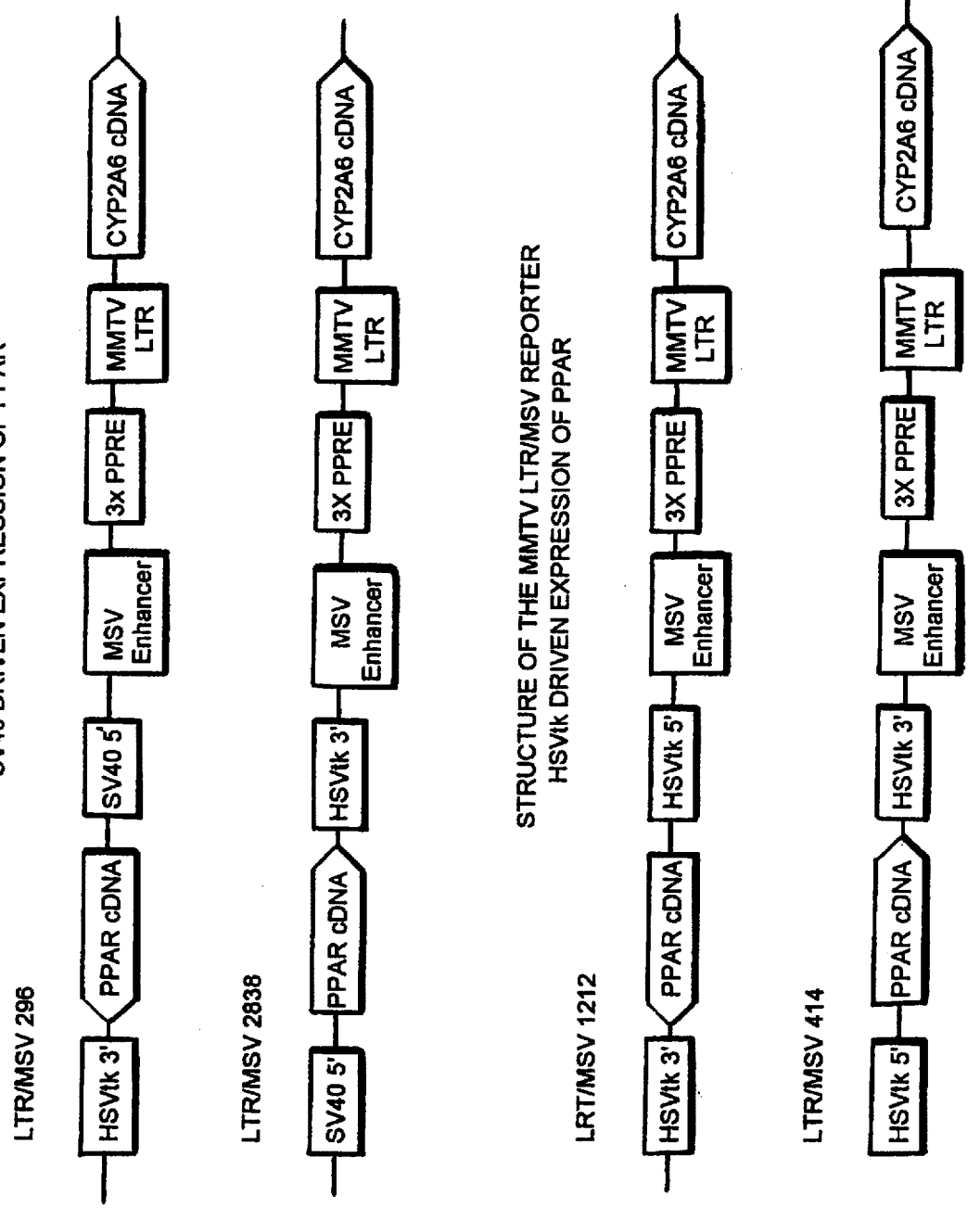
FIG. 3. Structure of the MMTV LTR/MSV reporter SV40 Driven Expression of PPARα and of the HSVtk Driven Expression of PPARα.

The analogous HSVtk based constructions were digested with a restriction enzyme which cuts between the 3×PPRE and the truncated HSVtk promoter and with Spe I which cuts the vector in the Ori P sequence. The T194/144 construction was likewise digested with Spe I to cut in the Ori P sequence and with a restriction enzyme which cuts between the 1×PPRE in this construction and the truncated MMTV LTR promoter/TATA box. Ligation of the appropriate fragments gave the four constructions shown in FIG. 3. The LTR/MSV296 construction with head to head orientation of the SV40 driven PPARα expression cassette and the reporter construct gave the best response to clofibrate. This construction was selected for further characterization.

(3). Stability of expression from the MMTV LTR based reporters

We monitored the stability of clofibrate induction as a function of time in culture. Both the basal and the induced level of expression initially declined before reaching basically stable values. The fold induction was stable.

We recently adopted electroporation as the technique for transfection. Protoplast fusion had given transfection frequencies of about 0.1%. Electroporation gives transfection frequencies of up to 50%. As a result, cells are available for analysis much sooner after transfection. Transfectants were initially selected by exposure to 400 ug/ml of Hygromycin B. This concentration was later reduced to 100–200 ug/ml because even fully resistant cells grow more slowly in the presence of 400 ug/ml of Hygromycin B. There may be some decline from initial vector copy number and hence decline in expression. The electroporation protocol was performed as follows.

Centrifuged cells were resuspended in RPM1 Medium 1640+10% horse serum at about $1\times10^7$ cells/ml. 0.8 ml cells cuvette (BTX) (4 mm Gap) and a single pulse (BTX electro cell manipulator 600) in high voltage mode (2.5 kv/resistance) and resistance=R8 was applied. The cells were then transferred into a 25 cm² tissue culture flask and 10 ml media was added. The cell concentration was determined by electronic particle counting. One (or two) days post electroporation, cells were counted, diluted to about $1\times10^5$ cells/ml and 400 µg hygromycin B was added. The culture was incubated for 4 days. The cell concentration then was determined by electronic particle counting. If the cell concentration was greater than about $6\times10^5$ cells/ml the culture was assayed. If not, the culture was diluted with fresh media to about $2.5\times10^5$ cell/ml, 100 µg/ml Hygromicin was added and the cells were recounted in about 2 days. In general, this dilution scheme can be used for routine culture of plasmid-bearing cells.

We also simultaneously produced a series of similar constructions with a single copy of the ACO PPRE. Our previous experience with instability was that the effect was reversible by treatment with 5-aza-deoxycytidine which implicated CpG sequences as the cause. The additional ACO PPRE's were inserted with Kpn I linkers which can introduce CpG sequences. We were afraid that the constructions with the multiple PPRE's might prove unstable. As shown above that was not the case.

LTR/MSV296 #17/18 contains a single PPRE and its configuration is the same as the successful construction with multiple PPRE's. However, the inducibility of the constructs with a single PPRE was relatively unstable.

The apparent instability may indicate that the receptor binds to the DNA recognition sequence in the absence of ligand but does not activate transcription until ligand binds.

(4). Response to agents known to induce peroxisome proliferation.

A useful system to detect the ability of chemicals to induce peroxisome proliferation must obviously be able to correctly rank chemicals of known ability to induce peroxisome proliferation. The system described herein, as currently configured, does correctly rank the limited series of Wyeth 14,463, ciprofibrate and clofibrate.

(5). Further Characterization of the Preferred Embodiment and Extension to other Species The most successful reporter construct (i.e., that which results in the greatest signal to noise ratio and/or the lowest background in the above-described assay for measuring PPARα activation) is introduced into the high copy number vector (1-histidinol resistance) to increase the basal and/or induced levels of expression, thereby improving the daily variability in the assay while maintaining the fold inducibility. We know from past experience that expression of the receptor from the high copy number vector is toxic to the cells. Therefore the receptor expression cassette is co-transfected on the low copy number plasmid (hygromycin B resistance) to avoid toxicity.

Analogous constructions with the rat PPARα, the human PPARα and no PPARα (control) are prepared and constructed in accordance with the above-described protocols. For example, analogous constructs containing the rat PPARα or the human PPARα are prepared by substituting the sequence encoding these alternative PPARα for that encoding the mouse PPARα in the above-described Examples. Construction and testing of the analogous constructs in the above-described assay for measuring PPARα activation then is used to determine the extent of species differences, if any.

The utility of the system for testing chemicals of known ability to induce peroxisome proliferation is examined by testing a series of chemicals of known peroxisome proliferators including clofibrate, ciprofibrate, WY-14,463, trichloracetic acid, nafenopin and phthalate esters as well as the postulated endogenous fatty acid ligands, arachidonic acid and linoleic acid. Specificity is tested by examining ligands for other receptors such as glucocorticoids, mineralocorticoids, retinoids, phorbol esters and triiodothryonine as well as other chemicals believed not to bind to the receptor, such as dehydroepiandosterone and cholesterol (Gottlicher et al., *Proc. Natl. Acad. Sci. USA* 89:4653-4657 (1992)). Also, of particular interest are other non-genotoxic liver carcinogens from the NTP testing program. The influence of solvents which can be used to add the test agents, such as DMSO, ethanol and methanol also is tested in order to determine appropriate limits on concentration.

The simplicity of the assay procedure and automation of the plate scoring procedure greatly facilitates the testing aspects as well as the development aspects. It is possible to completely evaluate the concentration response data for one compound in a panel of cell lines using a single 96 well plate. The use of multiple plates for replicate determinations is desireable and will be performed. The control cell lines: constitutive reporter (reporter inhibition), inducible reporter (cytotoxicity) and PPRE-reporter without functional PPARα as well as cells containing the mouse, rat and human receptors are each aliquotted into a 12 well row of the plate (six of the eight rows used). The remaining two rows can be used as blanks and calibration curves for product standards.

The test agent is added to the first well in each row and serially diluted to the tenth row. The two remaining rows of cells are negative controls. The plates are incubated the required length of time and the amount of product analyzed. Each chemical is tested on at least two independent days and the results analyzed in order to determine the reproducibility of the response.

Appropriate statistical methods for analysis of the results are easily identified. For example, some variation of trend analysis is appropriate to determine whether a response is statistically significant. The testing of negative compounds helps to establish any biologically-based limit of significance. The frequency of false positive and false negative response is determined for the system with rodent receptors using chemicals of known peroxisome proliferating activity in rodents.

Appropriate methods for comparing the results of assays with the same chemical conducted on different days are developed. The system and protocol have sufficient reproducibility to allow pooling of the assays results from independent experiments during analysis. Alternatively, results from independent days are normalized using the basal level of reporter activity and the amount of reporter activity observed at a fixed concentration of positive control compound (e.g. clofibrate). The responses in independent experiments then are scaled and pooled.

Given the potential variability in receptor levels in cell lines containing receptors from different species, species-specific effects are analyzed by comparing the rank order (concentration to induce a particular increase in reporter levels) of the chemicals in cells containing the mouse, rat and human receptors. Comparison of the rank order between the mouse and rat (where data exist or could be obtained on in vivo effects) are used to establish the appropriateness of this approach. The performance of the human receptor is of particular interest with respect to the toxicological significance of these agents to humans. The availability of this system will help to clarify potential effects in humans as well as allow identification (early in development) of chemicals which may present safety assessment problems (yield a positive response in rodent models).

Example IV

Vector Construction

Construction of p91DΔEH#7

The CYP2A6 expression plasmid p91Dtk (Davies et.al., [1989] *Carcinogenesis* 10: 885-91) was digested to completion with Hind III and partially digested with Eco RI (Note that at that time, CYP2A6 was designated as P450IIA3). A fragment containing a 1.1 kb deletion was agarose gel purified. This fragment was ligated to the Hind III—Eco RI polylinker of pUC 19 (NE Biolabs). The plasmid p91DΔEH clone #7 had the desired removal of the OCT enhancer and the D2 and D3 elements of the HSV tk promoter with retention of the TATA box. (Mcknight, 1980, Nucleic Acids Research 8: 5949-5964). p91DtkΔEH #7 has a minimal (truncated) HSVtk promoter and can be used to test DNA sequences for enhancer activity.

Construction of p91DΔEH#6

The CYP2A6 expression plasmid p91Dtk (Davies et.al., [1989] *Carcinogenesis* 10: 885-891) was digested to completion with Hind III and partially digested with Eco RI (Note that at that time, CYP2A6 was designated as P450IIA3). A fragment containing a 1.2 kb deletion was agarose gel purified. This fragment was ligated to the Hind III—Eco RI polylinker of pUC19 (NE Biolabs). This plasmid, p91DΔEH clone #6, had the entire HSV tk promoter removed. (The Eco RI site cut immediately precedes the ATG in the CYP2A6 coding sequence). p91DtkΔEH #6 has no promoter sequences whatsoever. It can be used to test DNA sequences for the presence of a putative promoter and/or to test the relative strength of a known promoter (which by definition has a TATA box).

Construction of T194

L15CAT is pBLCAT2 (Luckow et.al., 1987 Nucleic Acid Research 15: 5490) in which the Hind III to Bam HI segment of the polylinker has been removed and replaced by the sequence of SEQ. ID No. 10. (Sher et.al., 1993 Biochemistry 32: 5598–5604). This gives a polylinker whose restriction sequence is Hind III, Sal I, Eco RV, Spe I, Xba I, Bgl II, Pst I, Mlu I, Bcl I, Sac II, Bam HI.

The rat ACO PPRE was isolated with 5' Hind III and 3' Sal I ends by PCR of rat cellular DNA (Sher et.al., 1993 Biochemistry 32: 5598–5604) and ligated into Hind III/Sal I digested L15CAT. The fragment containing the ACO PPRE and the "minimal tk promoter" of L15CAT was obtained by digestion with Hind III and Xho I. The "minimal tk promoter" of L15CAT is larger than the "minimal tk promoter" of p91DΔEH#7 in that it also contains the D2 and D3 elements. The fragment was then ligated into p91DΔEH#6 which had been digested with Hind III and Sal I. This plasmid was then digested with Hind III, blunt ended with Klenow and linkered with Xho I linkers.

The mouse PPARα cDNA was obtained by PCR with Bam HI ends from total mouse RNA (Sher et. al., 1993 Biochemistry 32: 5598–5604). This product was ligated into the Bam HI cloning site of pSG5. The SV40 expression cassette was then excised from pSG5 by Sal I digestion and ligated into the Xho I site of the above plasmid. A clone with the SV40 mouse PPARα expression cassette in head to head orientation relative to CYP2A6 cDNA was designated T194.

Construction of T144 p91DΔEH#6 was digested with Hind III and Sal I and ligated to the Hind III/Sal I fragment of the MMTV LTR obtained from pMAM-neo (Clontech). This plasmid was cut with Hind III and blunt ended with Klenow. The 0.5 kb Bam HI fragment of the HaMSV enhancer (Ostrowski et.al., 1984, EMBO Journal 3:1891–1899) was isolated, blunt ended with Klenow and ligated into the plasmid. A clone with 5' to 3' orientation of HaMSV with respect to the MMTV LTR and CYP2A6 cDNA was designated cl 25. A clone with the opposite orientation was designated cl 23.

Glucocorticoid induced expression of CYP2A6 in cl 25 decreased with time in culture but could be restored by treatment with 5-aza-deoxycytidine. This suggested that methylation of CpG sites was responsible for the loss of responsiveness. cl 25 was digested with Avr II and Sal I to remove bp 133 to 1555 of the MMTV LTR. This fragment was replaced with a PCR generated fragment of the MMTV LTR containing bp 133 (Avr II) to bp 1306 with the addition of a Sal I end. This process removed a sequence containing multiple CpG sequences. The resulting construct was designated T144. Glucocorticoid induced expression of CYP2A6 in T144 was stable with time in culture.

Construction of T194/T144

T144 was digested to completion with Spe I and partially digested with Sac I. The fragment containing the CYP2A6 cDNA and the now truncated MMTV LTR (the glucocorticoid response element was removed by this process) was isolated by agarose gel purification. T194 was digested with Sal I, blunt ended with Klenow, linkered with Sac I linkers, digested to completion with SpeI and partially digested with Sac I. The fragment containing the ACO PPRE, and the SV40 PPARα expression cassette was isolated by agarose gel purification. These two fragments were 1 ligated together to give T194/T144.

Construction of SV40 Expression Cassette

The SV40 expression cassette was derived from pSG5 (Stratagene). The polylinker for cDNA expression was removed by digestion with Eco RI and Bgl II. It was replaced by complimentary oligos 275A (SEQ. ID No. 11) and 275B (SEQ. ID No. 12). This restored the Eco RI site, destroyed the Bgl II site and added Xba I, Xho I and Hind III sites. The SV40 expression cassette was removed by digestion with Sal I, blunt ended with Klenow and modified by the addition of Cla I linkers.

Construction of p2A6plSV#29 mp#6

A portion of the polylinker in p91DΔEH #7 was removed by digestion to completion with Hind III and partial digestion with Kpn I. The polylinker sequence was replaced by the complimentary oligos 91DEH-B2 (SEQ. ID No. 13) and 91DEH-A2 (SEQ. ID No. 14). This added Nhe I, Bgl II, Not I and Cla I sites while removing Hind III, Sph I, Pst I, Bsp MI, Sal I, Xba I, Bam HI and Sma I sites. The Kpn I site was restored.

The vector with the modified polylinker was digested with Cla I and the SV40 expression cassette was inserted. The orientation of the SV40 cassette with respect to CYP2A6 was head to head.

Construction of p2A6pLSV296.T23 (mp#17)

The mouse PPARα cDNA was obtained by PCR with Bam HI ends from total mouse RNA (Sher et.al., 1993 Biochemistry 32: 5598–5604) and inserted into the Bam HI site of Bluescript CAT (Stratagene) to get T23.

The mouse PPARα was removed from T23 by digestion with Bam HI. The fragment was blunt ended with Klenow, Xba I linkers were added and the resulting fragment was ligated into the Xba I site of p2A6plSV#29 mp#6. The orientation of the cDNA was confirmed.

Construction of a Reporter with Multiple PPREs: Addition of Three Copies of the Rat Acyl CoA Oxidase DNA Response Element (ACO PPRE)

T194 was digested to completion with Spe I and was ligated to p91DtkΔEH#7 to make p91DtkΔEH#7 mp9.2. This construction contained one copy of the ACO PPRE (from T194). It was partially digested with Kpn I and DNA with a single cut was isolated by agarose gel electrophoresis.

Additional copies of the ACO PPRE were obtained by PCR of T194 followed by Kpn I digestion of the product using the primers identified as SEQ. ID Nos. 15 and 16. The Kpn digested PCR product was ligated into the singly cut p91DtkΔEH#7 mp9.2. One clone with an additional copy of the ACO PPRE inserted into the correct position (T194ΔEH#7 mp9.2 Aco #43) was chosen. This clone was again partially digested with Kpn I, singly cut DNA was isolated by agarose gel electrophoresis, and ligated to the Kpn I digested PCR product. One clone with a third ACO PPRE in the correct position, T194ΔEH#7 mp9.2 ACO$^{2\ \#16}$, was utilized for the next step.

A fragment containing 3 copies of the ACO PPRE was obtained by digesting T194ΔEH#7 mp9.2 ACO$^2$ #16 with Pvu II, adding Nhe I linkers, digesting with Ecl 136 and adding Not I linkers. This fragment was ligated into p2A6pLSV296.T23 (mp #17) which had been digested with Nhe I and Not I. A clone with the correct insertion was designated p2A6pLSV296.T23 Aco$^2$ #16.

Addition of the Harvey Murine Sarcoma Virus (HaMSV) Enhancer

T144 was digested with Ssp I and partially digested with Nar I. The fragment containing the HaMSV enhancer, MMTV LTR, CYP2A6 cDNA and the 3' HSVtk sequences was isolated by agarose gel electrophoresis. pEBVHis (Crespi et.al., 1990 *Mutation and the Environment*, Part B: 97–106, Wiley-Liss Inc.) was digested with Hind III, blunt ended with Klenow, linkered with Cla I linkers, digested with Nhe I, blunt ended with Klenow and digested with Cla I. These fragments were ligated to get pEH T144. Unexpectedly, the orientation obtained for the CYP2A6 cDNA with respect to the HisD cDNA was head to head.

A fragment containing the HaMSV enhancer was obtained by digesting pEH T144 with Avr II. This fragment was ligated into the Nhe I site of p2A6pLSV296.T23 Aco$^2$ #16. Two clones with the correct insertion were designated p2A6pLSV296.T23 Aco$^2$ #16 MSV #53 and #58. Replacement of the ΔHSVtk promoter with the Truncated Mouse Mammary Tumor Virus Long Terminal Repeat (ΔMMTV LTR)

An 8.8 kb fragment of p2A6pLSV296.T23 Aco$^2$ #16 MSV #53 was isolated after complete digestion with Spe I and partial digestion with Sac I. This fragment contained the mouse PPARα SV40 expression cassette, the HaMSV enhancer and the three copies of the ACO PPRE. A 4 kb fragment of T194/T144 was obtained after digestion with Spe I and Sac I. This fragment contained the ΔMMTV LTR, and the CYP2A6 cDNA with its polyadenylation signal. These two fragments were ligated together.

Two clones with the desired configuration were isolated. These were designated T194/T144 296 MSV #37 and #39. The results from these two were pooled in EXAMPLE III and referred to as LTR/MSV296 #37/39.

---

We claim:

1. A method for detecting the formation of a receptor-ligand complex in a cell, the method involving:
   (1) contacting a ligand with a cell that expresses a receptor specifically reactive with the ligand, under conditions to permit formation of the receptor-ligand complex, wherein the cell contains:
      (a) a reporter cassette for detecting formation of the receptor-ligand complex, the reporter cassette including a DNA sequence encoding a cytochrome P450 operatively coupled to a promoter, a DNA-responsive element and a polyadenylation signal sequence, wherein the DNA responsive element is responsive to a DNA-binding element present in a receptor-ligand complex, and
      (b) a cytochrome P450 catalysis system;
   (2) contacting the cell with a substrate for the cytochrome P450 catalysis system under conditions to permit catalysis of the substrate by the cytochrome P450 catalysis system to form a cytochrome P450 catalysis system product; and
   (3) detecting the cytochrome P450 catalysis system product, wherein the formation of the cytochrome P450 catalysis system product is indicative of the formation of the receptor-ligand complex wherein the reporter cassette is contained on plasmid pT194/T144 296 MSV #39 as contained in the host cell having ATCC No. CRL 11978.

2. A reporter cassette for detecting the formation of a receptor-ligand complex in a mammalian cell, comprising:

at least one DNA sequence encoding a cytochrome P450 with a polyadenylation signal sequence operatively coupled to each of a promoter sequence and a DNA responsive element, wherein the DNA responsive element is responsive to a DNA-binding element present in the receptor-ligand complex, wherein the reporter cassette is contained on plasmid pT194/T144 296 MSV #39 as contained in the host cell having ATCC No. CRL 11978.

3. A plasmid vector comprising a reporter cassette for detecting the formation of a receptor-ligand complex in a mammalian cell, wherein the plasmid vector is plasmid pT194/T144 296 MSV #39 as contained in the host cell having ATCC No. CRL 11978.

4. A cell containing the plasmid vector of claim 3.

5. A host cell containing plasmid pT194/T144 296 MSV #39 as contained in the host cell having ATCC No. CRL 11978.

* * * * *

UNITED STATES PATENT AND TRADEMARK OFFICE
CERTIFICATE OF CORRECTION

PATENT NO. : 5,726,041
DATED : March 10, 1998
INVENTOR(S) : Crespi et al.

It is certified that error appears in the above-identified patent and that said Letters Patent is hereby corrected as shown below:

On the title page, item [19] and item [75] Inventors name, please delete "Chrespi" and replace --Crespi-- therefore.

Signed and Sealed this

Ninth Day of March, 1999

Attest:

Q. TODD DICKINSON

*Attesting Officer*  *Acting Commissioner of Patents and Trademarks*